United States Patent
Ohtani et al.

(10) Patent No.: US 6,787,545 B1
(45) Date of Patent: Sep. 7, 2004

(54) PYRROLOTRIAZINE DERIVATIVES HAVING SPLA2-INHIBITORY ACTIVITIES

(75) Inventors: Mitsuaki Ohtani, Osaka (JP); Masahiro Fuji, Osaka (JP); Tomoyuki Ogawa, Osaka (JP)

(73) Assignee: Shiongi & Co., Ltd., Osaka (JP)

( * ) Notice: Subject to any disclaimer, the term of this patent is extended or adjusted under 35 U.S.C. 154(b) by 175 days.

(21) Appl. No.: 10/049,912

(22) PCT Filed: Aug. 10, 2000

(86) PCT No.: PCT/JP00/05357

§ 371 (c)(1),
(2), (4) Date: Feb. 20, 2002

(87) PCT Pub. No.: WO00/21563

PCT Pub. Date: Apr. 20, 2000

(30) Foreign Application Priority Data

Aug. 23, 1999 (JP) .......................................... 11-235957

(51) Int. Cl.[7] .................... C07D 487/04; A61K 31/153; A61P 29/00

(52) U.S. Cl. ...................................... 514/243; 544/183

(58) Field of Search .......................... 544/183; 514/243

(56) References Cited

FOREIGN PATENT DOCUMENTS

| | | |
|---|---|---|
| EP | 0 620 214 A1 | 4/1994 |
| EP | 0 620 215 A1 | 10/1994 |
| EP | 0 675 110 A1 | 10/1995 |
| EP | 1 085 021 A1 | 3/2001 |
| EP | 1 157 704 A1 | 11/2001 |
| WO | WO 96/03120 A1 | 2/1996 |
| WO | WO 96/03376 A1 | 2/1996 |
| WO | WO 96/03383 A1 | 2/1996 |
| WO | WO 97/21664 A1 | 6/1997 |
| WO | WO 97/21716 A1 | 6/1997 |
| WO | WO 98/18464 A1 | 5/1998 |
| WO | WO 98/24437 A1 | 6/1998 |
| WO | WO 98/24756 A1 | 6/1998 |
| WO | WO 98/24974 A1 | 6/1998 |
| WO | WO 98/25609 A1 | 6/1998 |
| WO | WO 99/24026 A2 | 5/1999 |
| WO | WO 99/24033 A1 | 5/1999 |
| WO | WO 99/51605 A1 | 10/1999 |
| WO | WO 99/59999 A1 | 11/1999 |
| WO | WO 00/21563 A1 | 4/2000 |

OTHER PUBLICATIONS

Lin et al., J. Rheumatol. 23(7): 1162–1166, 1996.*
Lin et al., Inflammation 22(2): 161–173, 1998.*
Reynolds et al., "Analysis of Human Synovial Fluid Phospholipase A₂ on Short Chain Phosphatidylcholine–Mixed Micelles: Development of a Spectrophotometric Assay Suitable for a Microtiterplate Reader", *Analytical Biochemistry*, 204, 190–197 (1992), Academic Press, Inc., California, USA.

Yamawaki et al., "Synthesis and aldose reductase inhibitory activity of acetic acid derivatives of pyrrolo[1,2–c]imidazole", *Eur J Med Chem,* 28, 481–498 (1993), Elsevier, Paris.

Krause, O–Mesitylenesulfonylhydroxylamine, *Synthesis* (Oct. 8, 1971).

Patil et al., "Synthesis of Pyrrolo[2,1–f][1,2,4]triazine Congeners of Nucleic Acid Purines via the N–Amination of 2–Substituted Pyrroles [1]", *J. Heterocyclic Chem.,* 31, 781–786 (Jul.–Aug. 1994), Department of Oncology, Montefiore Medical Center, Bronx, New York, USA.

Hagishita et al., "Potent Inhibitors of Secretory Phospholipase A2: Synthesis and Inhibitory Activities of Indolizine and Indene Derivatives", *J. Med. Chem.,* 39, 3636–3658 (1996), American Chemical Society, USA.

Bailey et al., "Ethyl Pyrrole–2–Carboxylate", *Organic Syntheses,* pp. 618–619.

Flitsch et al., "Zur Chemie der 1–Amino–pyrrole," *Chem. Ber.,* 102, 3268–3276 (1969), Aus dem Organisch–Chemischen Institut der Universität Münster (Westf.).

* cited by examiner

*Primary Examiner*—Mukund Shah
*Assistant Examiner*—Venkataraman Balasubramanian
(74) *Attorney, Agent, or Firm*—Foley & Lardner

(57) ABSTRACT

The present invention provides a compound having sPLA₂ inhibiting activity.

The compound represented by the formula (I):

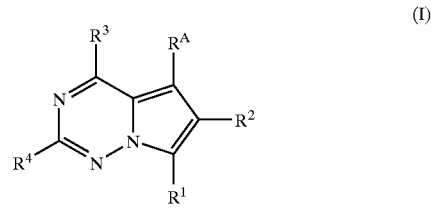

(I)

wherein $R^1$ is C1 to C20 alkyl, C2 to C20 alkenyl, C2 to C20 alkynyl, carbocyclic groups, heterocyclic groups or the like; $R^2$ is a hydrogen atom or a group containing 1 to 4 non-hydrogen atoms; $R^A$ is —COCONH₂ or the like; $R^3$ is -($L^2$)-(acidic group) wherein $L^2$ is a group connecting with an acid group; $R^4$ is a hydrogen atom or the like, its prodrug, their pharmaceutically acceptable salt, or solvate thereof.

14 Claims, No Drawings

PYRROLOTRIAZINE DERIVATIVES HAVING SPLA2-INHIBITORY ACTIVITIES

TECHNICAL FIELD

The present invention relates to a pyrrolotriazine derivative effective for inhibiting sPLA$_2$-mediated fatty acid release.

BACKGROUND ART sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arterial sclerosis, stroke, cerebral infarction, inflammatory colitis, psoriasis, heart failure, cardiac infarction, and the like. The participation of sPLA$_2$ is considered to be extremely wide and, besides, its action is potent.

Examples of sPLA$_2$ inhibitors include compounds described in EP-620214 (JP Laid-Open No. 010838/95, U.S. Pat. No. 5,578,634), EP-620215 (JP Laid-Open No. 025850/95, U.S. Pat. No. 5,684,034), EP-675110 (JP Laid-Open No. 285933/95, U.S. Pat. No. 5,654,326), WO 96/03120 (JP Laid-Open No. 505336/98), WO 96/03376 (JP Laid-Open No. 503208/98, U.S. Pat. No. 5,641,800), WO 96/03383 (JP Laid-Open No. 505584/98), WO 97/21664 (EP-779271), WO 97/21716 (EP-779273), WO 98/18464 (EP839806), WO98/24437(EP846687), WO98/24756, WO98/24794, W098/25609, W099/51605, W099/59999 and the like, or parabromophenacylbromide, mepacrine, manoaride, theilocien A$_1$ and the like.

DISCLOSURE OF INVENTION

The object of the present invention is to provide pyrrolotriazine derivatives having sPLA$_2$ inhibitory activity and being useful for treatment of septic shock, adult respiratory distress syndrome, pancreatitis, injuries, bronchial asthma, allergic rhinitis, rheumatoid arthritis, arterial sclerosis, stroke, cerebral infarction, inflammatory colitis, psoriasis, heart failure, and cardiac infarction.

The present invention relates to I) a compound represented by the formula (I):

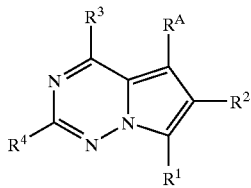

wherein R$^1$ is (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, or (c)-(L$^1$)-R$^5$ wherein L$^1$ is a divalent linking group of 1 to 18 atom(s) selected from hydrogen atom(s), nitrogen atom(s), carbon atom(s), oxygen atom(s), and sulfur atom(s), and R$^5$ is a group selected from the groups (a) and (b);

R$^2$ is a hydrogen atom or a group containing 1 to 4 non-hydrogen atoms;

R$^A$ is a group represented by the formula:

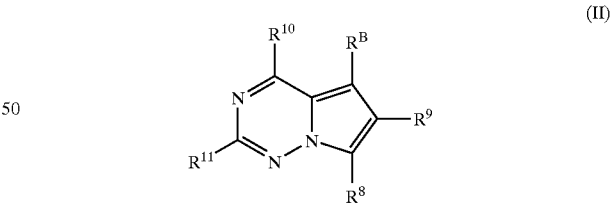

wherein R$^6$ and R$^7$ are independently a hydrogen atom, C1 to C3 alkyl, or a halogen; G$^1$ and G$^2$ are independently an oxygen atom or a sulfur atom; and G$^3$ is —NH$_2$ or —NHNH$_2$;

R$^3$ is —(L$^2$)—(acidic group) wherein L$^2$ is an acid linker having an acid linker length of 1 to 5;

R$^4$ is a hydrogen atom, C1 to C6 alkyl, aryl, a halogen or aralkyl, its prodrug, their pharmaceutically acceptable salt, or solvate thereof.

In more detail, the present invention relates to II) to XVII).

II) A compound represented by the formula (II):

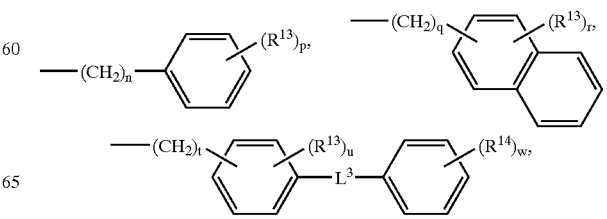

wherein R$^8$ is —(CH$_2$)$_m$—R$^{12}$ wherein m is an integer from 1 to 6, and R$^{12}$ is (d) a group represented by the formula:

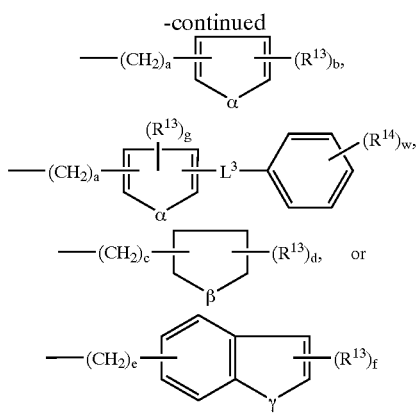

wherein a, c, e, n, q, and t are independently an integer from 0 to 2; $R^{13}$ and $R^{14}$ are independently selected from the group consisting of a halogen, C1 to C10 alkyl, C1 to C10 alkyloxy, C1 to C10 alkylthio, aryl, heterocyclic groups, and C1 to C10 haloalkyl; a is an oxygen atom or a sulfur atom; $L^3$ is —(CH$_2$)v—, —C=C—, —C≡C—, —O—, or —S— wherein v is an integer from 0 to 2; β is —CH$_2$— or —(CH$_2$)$_2$—; γ is an oxygen atom or a sulfur atom; b is an integer from 0 to 3; d is an integer from 0 to 4; f, p, and w are independently an integer from 0 to 5; g is an integer from 0 to 2; r is an integer from 0 to 7; and u is an integer from 0 to 4, or (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen;

$R^9$ is C1 to C3 alkyl, C2 to C3 alkenyl, C3 to C4 cycloalkyl, C3 to C4 cycloalkenyl, C1 to C2 haloalkyl, C1 to C3 alkyloxy, or C1 to C3 alkylthio;

$R^{10}$ is -(L$^4$)-$R^{15}$ wherein $L^4$ is represented by the formula:

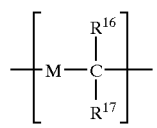

wherein M is —CH$_2$—, —O—, —N($R^{18}$)—, or —S—; $R^{16}$ and $R^{17}$ are independently a hydrogen atom, C1 to C10 alkyl, aryl, aralkyl, carboxy, or a halogen, and $R^{18}$ is a hydrogen atom or C1 to C6 alkyl; and $R^{15}$ is represented by the formula:

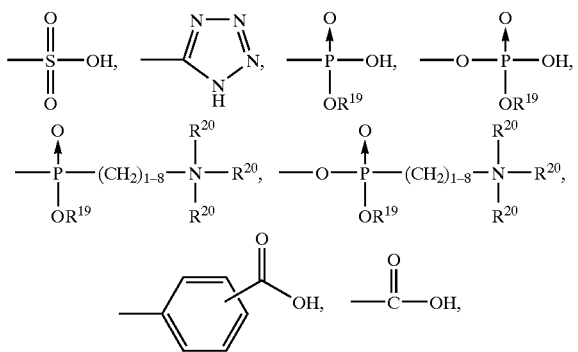

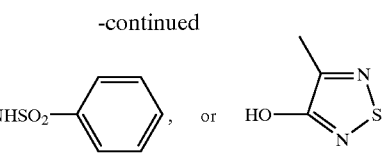

wherein $R^{19}$ is a hydrogen atom, a metal, or C1 to C10 alkyl; $R^{20}$ is independently a hydrogen atom or C1 to C10 alkyl; h is an integer from 1 to 8;

$R^{11}$ is a non-interfering substituent selected from the group consisting of a hydrogen atom, C1 to C8 alkyl, C2 to C8 alkenyl, C2 to C8 alkynyl, C7 to C12 aralkyl, C3 to C8 cycloalky, C3 to C8 cycloalkenyl, phenyl, tolyl, xylyl, biphenylyl, C1 to C8 alkyloxy, C2 to C8 alkenyloxy, C2 to C8 alkynyloxy, C2 to C12 alkyloxyalkyl, C2 to C12 alkyloxyalkyloxy, C2 to C12 alkylcarbonyl, C2 to C12 alkylcarbonylamino, C2 to C12 alkyloxyamino, C2 to C12 alkyloxyaminocarbonyl, C1 to C12 alkylamino, C1 to C6 alkylthio, C2 to C12 alkylthiocarbonyl, C1 to C8 alkylsulfinyl, C1 to C8 alkylsulfonyl, C2 to C8 haloalkyloxy, C1 to C8 haloalkylsulfonyl, C2 to C8 haloalkyl, C1 to C8 hydroxyalkyl, —C(O)O(C1 to C8 alkyl), —(CH$_2$)z-O—(C1 to C8 alkyl), benzyloxy, aryloxy, aryloxy C1 to C8 alkyl, arylthio, arylthio C1 to C8 alkyl, cyano C1 to C8 alkyl, —(CONHSO$_2$R$^{21}$) wherein $R^{21}$ is C1 to C6 alkyl or aryl, formyl, amino, amidino, halogen, carboxy, —(CH$_2$)z-COOH wherein z is an integer from 1 to 8, cyano, cyanoguanidyl, guanidino, hydrazide, hydrazino, hydroxy, hydroxyamino, nitro, phosphono, and —SO$_3$H; and $R^B$ is a group represented by the formula:

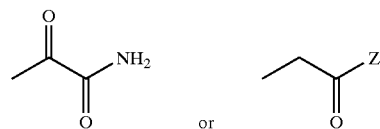

wherein Z is —NH$_2$ or —NHNH$_2$, its prodrug, their pharmaceutically acceptable salt, or solvate thereof.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

—CH$_2$— and —(CH$_2$)$_2$— in β may be substituted with $R^{13}$.

III) A compound, its prodrug, their pharmaceutically acceptable salt, or solvate thereof as described in above I) or II), wherein said $R^1$ and $R^8$ are represented by the formula:

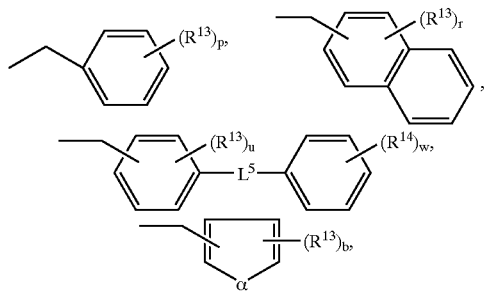

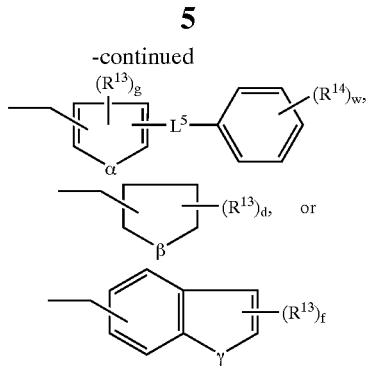

wherein $R^{13}$, $R^{14}$, b, d, f, g, p, r, u, w, α, β, and γ are as defined above; $L^5$ is a bond, —CH$_2$—, —C=C—, —C≡C—, —O—, or —S—.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

—CH$_2$— and —(CH$_2$)$_2$— in β may be substituted with $R^{13}$.

IV) A compound, its prodrug, their pharmaceutically acceptable salt, or solvate thereof as described in any one of I) to III), wherein said $R^2$ and $R^9$ are C1 to C3 alkyl or C3 to C4 cycloalkyl.

V) A compound, its prodrug, their pharmaceutically acceptable salt, or solvate thereof as described in any one of I) to IV), wherein said $L^2$ and $L^4$ are —O—CH$_2$—.

VI) A compound represented by the formula (III):

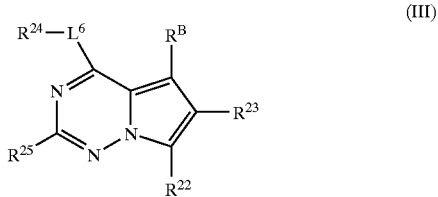

(III)

wherein $R^{22}$ is a group represented by the formula:

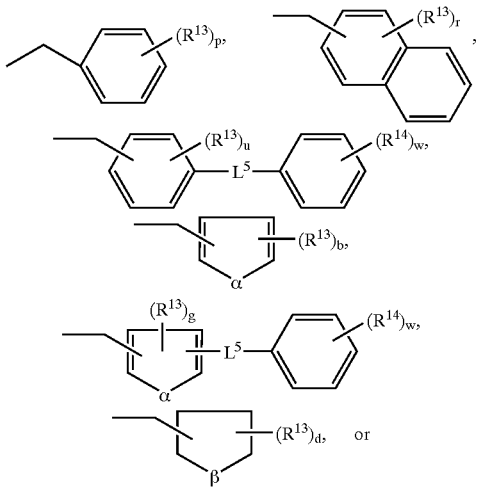

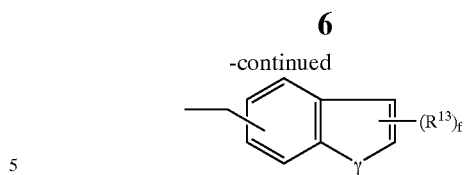

wherein $L^5$ is a bond, —CH$_2$—, —C=C—, —C≡C—, —O—, or —S—; $R^{13}$ and $R^{14}$ are independently selected from a group consisting of a halogen, C1 to C10 alkyl, C1 to C10 alkyloxy, C1 to C10 alkylthio, aryl, heterocyclic groups, and C1 to C10 haloalkyl; b is an integer from 0 to 3; d is an integer from 0 to 4; f, p, and w are independently an integer from 0 to 5; g is an integer from 0 to 2; r is an integer from 0 to 7; u is an integer from 0 to 4; α is an oxygen atom or a sulfur atom; β is —CH$_2$—or —(CH$_2$)$_2$—; and γ is an oxygen atom or a sulfur atom;

$R^{23}$ is C1 to C3 alkyl or C3 to C4 cycloalkyl;

$L^6$ is —O—CH$_2$—, —S—CH$_2$, —N($R^{26}$)—CH$_2$—, —CH$_2$—CH$_2$—, —O—CH(CH$_3$)—, or —O—CH((CH$_2$)$_2$Ph)— wherein $R^{26}$ is a hydrogen atom or C1 to C6 alkyl, Ph is pheny;

$R^{24}$ is —COOH, —SO$_3$H, or P(O)(OH)$_2$;

$R^{25}$ is a hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, a halogen, carboxy, C1 to C6 alkyloxycarbonyl, aryloxy, aryloxy C1 to C8 alkyl, arylthio, arylthio C1 to C8 alkyl, cyano C1 to C8 alkyl, carbocyclic groups, or heterocyclic groups; and $R^B$ is a group represented by the formula:

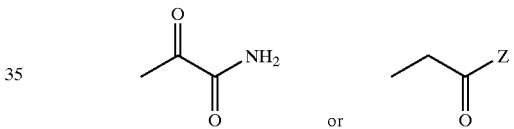

wherein Z is —NH$_2$ or —NHNH$_2$, its prodrug, their pharmaceutically acceptable salt, or solvate thereof.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

—CH$_2$— and —(CH$_2$)$_2$— in β may be substituted with $R^{13}$.

VII) A compound represented by the formula (IV):

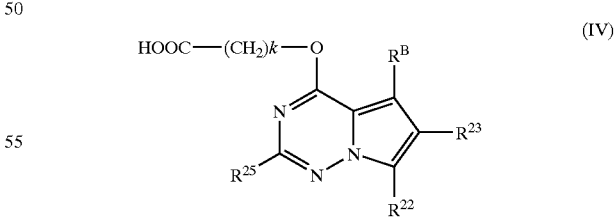

(IV)

wherein $R^{22}$ is a group represented by the formula:

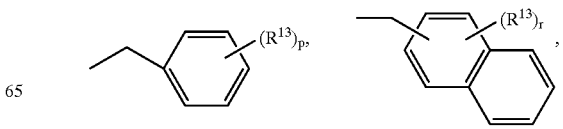

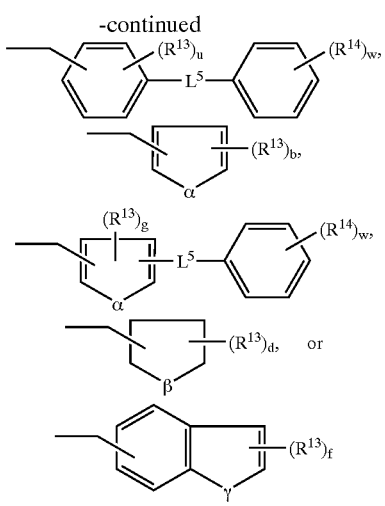

wherein L⁵ is a bond, —CH₂—, —C=C—, —C≡C—, —O—, or —S—; R¹³ and R¹⁴ are independently selected from the group consisting of a halogen, C1 to C10 alkyl, C1 to C10 alkyloxy, C1 to C10 alkylthio, aryl, heterocyclic groups, and C1 to C10 haloalkyl; b is an integer from 0 to 3; d is an integer from 0 to 4; f, p, and w are independently an integer from 0 to 5; g is an integer from 0 to 2; r is an integer from 0 to 7; u is an integer from 0 to 4; α is an oxygen atom or a sulfur atom; β is —CH₂— or —(CH₂)₂—; and y is an oxygen atom or a sulfur atom;

R²³ is C1 to C3 alkyl or C3 to C4 cycloalkyl;

R²⁵ is a hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, a halogen, carboxy, C1 to C6 alkyloxycarbonyl, aryloxy, aryloxy C1 to C8 alkyl, arylthio, arylthio C1 to C8 alkyl, cyano C1 to C8 alkyl, carbocyclic groups, or heterocyclic groups;

R$^B$ is a group represented by the formula:

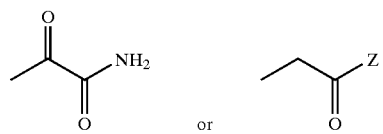

wherein Z is —NH₂ or —NHNH₂;
and k is an integer from 1 to 3, its prodrug, their pharmaceutically acceptable salt, or solvate thereof.

When the above b, d, f, p, r, u, and/or w are 2 or more, a plural number of R¹³ or R¹⁴ may be different from one another. When R¹³ is a substituent on the naphthyl group, the substituent may be substituted at any arbitrary position on the naphthyl group.

—CH₂— and —(CH₂)₂— in β may be substituted with R¹³.

VIII) A compound, its prodrug, their pharmaceutically acceptable salt, or solvate thereof as described in VI), wherein said L⁶ is —O—CH₂—.

IX) A compound, its prodrug, their pharmaceutically acceptable salt, or solvate thereof as described in any one of I) to VIII), wherein said R$^A$ and R$^B$ are —COCONH₂.

X) A compound, its prodrug, their pharmaceutically acceptable salt, or solvate thereof as described in any one of I) to VIII), wherein said R$^A$ and R$^B$ are —CH₂CONH₂.

XI) A compound, its prodrug, their pharmaceutically acceptable salt, or solvate thereof as described in any one of I) to VIII), wherein said R$^A$ and R$^B$ are —CH₂CONHNH₂.

XII) A prodrug as described in any one of I) to XI), wherein the prodrug is an ester prodrug.

XIII) A pharmaceutical composition containing a compound as described in any one of I) to XII) as an active ingredient.

XIV) A pharmaceutical composition as described in XIII), which is for inhibiting sPLA₂.

XV) A pharmaceutical composition as described in XIII), which is for treatment or prevention of inflammatory diseases.

XVI) Use of a compound of any one of I) to XI) for preparation of a pharmaceutical composition for treating inflammatory diseases.

XVII) A method for treating a mammal, including a human, to alleviate the pathological effects of inflammatory diseases, which comprises administration to said mammal of a compound as described in any one of I) to XI) in a pharmaceutically effective amount.

In the present specification, the term "alkyl" employed alone or in combination with other terms means a straight- or branched chain monovalent hydrocarbon group having a specified number of carbon atoms. An example of =the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooctyl), cycloalkenyl (such as cyclobutylenyl, cyclopentenyl, cyclohexenyl, cycloheptenyl, and cyclooctenyl), phenyl, spiro[5,5]undecanyl, naphthyl, norbornyl, bicycloheptadienyl, tolyl, xylyl, indenyl, stilbenyl, terphenylyl, diphenylethylenyl, phenylcyclohexenyl, acenaphthyl, anthryl, biphenylyl, and a phenylalkylphenyl derivative represented by the formula (V):

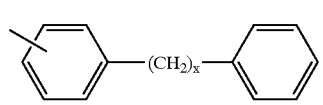

wherein x is an integer from 1 to 8.

The term "spiro[5,5]undecanyl" refers to the group represented by the formula:

Phenyl, C3 to C8 cycloalkyl or the like is preferred as a carbocyclic groups in the $R^4$.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, pyrrolidinyl, piperidinyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, 1,4-thioxanyl, azetidinyl, hexamethyleneiminium, heptamethyleneiminium, piperazinyl and the like.

Furyl, thienyl or the like is preferred as a heterocyclic group in the $R^{13}$ and $R^{14}$.

Preferred carbocyclic and heterocyclic groups in $R^1$ are (g) a group represented by the formula:

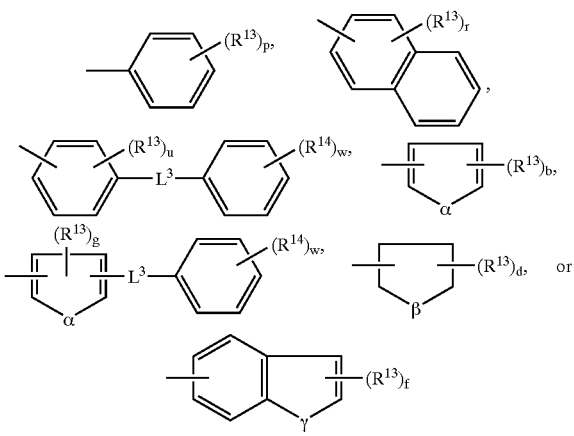

wherein $R^{13}$ and $R^{14}$ are independently selected from the group consisting of a halogen, C1 to C10 alkyl, C1 to C10 alkyloxy, C1 to C10 alkylthio, aryl, heterocyclic groups, and C1 to C10 haloalkyl, α is an oxygen atom or a sulfur atom, $L^5$ is —(CH$_2$)v-, —C=C—, —C≡C—, —O—, or —S— wherein v is an integer from 0 to 2, β is —CH$_2$— or —(CH$_2$)$_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4.

When the above b, d, f, p, r, u, and/or w are 2 or more, a plural number of $R^{13}$ or $R^{14}$ may be different from one another.

When $R^{13}$ is a substituent on the naphthyl group, the substituent may be substituted at any arbitrary position on the naphthyl group.

—CH$_2$— and —(CH$_2$)$_2$— in β may be substituted with $R^{10}$.

A more preferable example includes (h) a group represented by the formula:

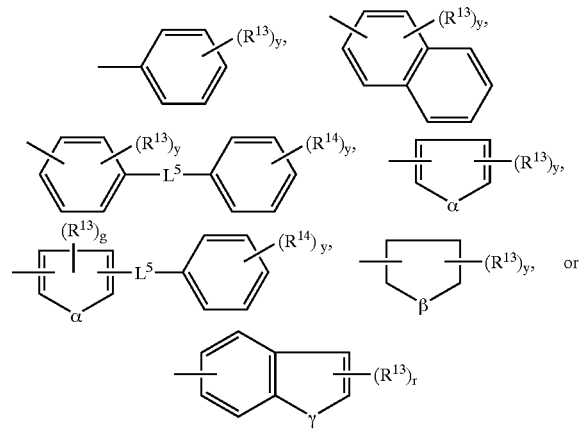

wherein $R^{13}$, $R^{14}$, α, β, and γ are the same as defined above, $L^5$ is —CH$_2$—, —C=C—, —C≡C—, —O—, or —S—, and y is 0 or 1.

When the above b, d, f, p, r, u, and/or w are 2 or more, a plural number of $R^{13}$ or $R^{14}$ may be different from one another.

When $R^{13}$ is a substituent on the naphthyl group, the substituent may be substituted at any arbitrary position on the naphthyl group.

—CH$_2$— and —(CH$_2$)$_2$— in β may be substituted with $R^{10}$.

The "pyrrolo[2,1-f][1,2,4]triazine nucleus" is represented by the following structural formula together its numerical ring position for substituent placement:

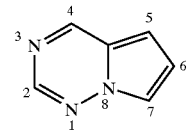

The term "non-interfering substituent" in the present specification means a group suitable for substitution of the above mentioned "carbocyclic group" and "heterocyclic group". An example of the non-interfering substituents includes C1 to C8 alkyl, C2 to C8 alkenyl, C2 to C8 alkynyl, C7 to C12 aralkyl (such as benzyl and phenethyl), C2 to C8 alkenyloxy, C2 to C8 alkynyloxy, C3 to C8 cycloalkyl, C3 to C8 cycloalkenyl, phenyl, tolyl, xylyl, biphenylyl, C1 to C8 alkyloxy, C2 to C12 alkyloxy alkyl (such as methyloxymethyl, ethyloxymethyl, methyloxyethyl, and ethyloxyethyl), C2 to C12 alkyloxyalkyloxy (such as methyloxymethyloxy and methyloxyethyloxy), C1 to C12 alkylcarbonyl (such as methylcarbonyl and ethylcarbonyl), C1 to C12 alkylcarbonylamino (such as methylcarbonylamino and ethylcarbonylamino), C1 to C12 alkyloxyamino (such as methyloxyamino and ethyloxyamino), C1 to C12 alkyloxyaminocarbonyl (such as methyloxyaminocarbonyl and ethyloxyaminocarbonyl), C1 to C12 alkylamino (such as methylamino, ethylamino, dimethylamino, and ethylmethylamino), C1 to C6 alkylthio, C1 to C12 alkylthiocarbonyl (such as methylthiocarbonyl and ethylthiocarbonyl), C1 to C8 alkylsulfinyl (such as methylsulfinyl and ethylsulfinyl), C1 to C8 alkylsulfonyl (such as methylsulfonyl and ethylsulfonyl), C2 to C8 haloalkyloxy (such as 2-chloroethyloxy and 2-bromoethyloxy), C1 to C8 haloalkylsulfonyl (such as chloromethylsulfonyl and bromomethylsulfonyl), C1 to C8 haloalkyl, C1 to C8 hydroxyalkyl (such as hydroxymethyl and hydroxyethyl), —C(O)O(C1 to C8alkyl) (such as methyloxycarbonyl and ethyloxycarbonyl), —(CH$_2$)z-O—(C1 to C8 alkyl) wherein z is an integer from 1 to 8, benzyloxy, aryloxy (such as phenyloxy), arylthio (such as phenylthio), —(CONHSO$_2$R$^{21}$) wherein R$^{21}$ is C1 to C6 alkyl or aryl, formyl, amino, amidino, halogen, carboxyl, —(CH$_2$)z-COOH (such as carboxymethyl, carboxyethyl, and carboxypropyl) wherein z is an integer from 1 to 8, cyano, cyanoguanidino, guanidino, hydrazide, hydrazino, hydroxy, hydroxyamino, nitro, phosphono, —SO$_3$H, carbocyclic groups, heterocyclic groups and the like.

Preferable are halogens, C1 to C6 alkyl, C1 to C6 alkyloxy, C1 to C6 alkylthio, C1 to C6 haloalkyl, and thienyl as the "non-interfering substituent" in the R$^1$. More preferable are halogens, C1 to C3 alkyl, C1 to C3 alkyloxy, C1 to C3 alkylthio, C1 to C3 haloalkyl, and thienyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to pyrrolo[2,1-f][1,2,4]triazine nucleus through a suitable linking atom (hereinafter defined as "acid linker").

An example of the acidic group includes (k) a group represented by the formula:

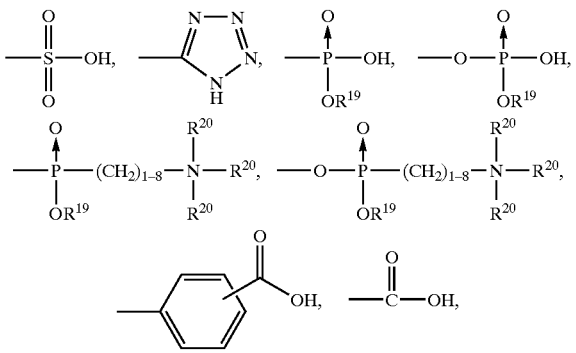

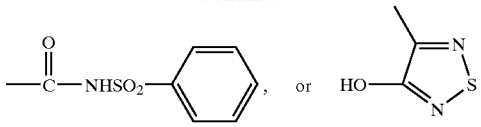

wherein R$^{19}$ is a hydrogen atom, a metal, or C1 to C10 alkyl; each R$^{20}$ is independently a hydrogen atom or C1 to C10 alkyl; h is is an integer from 1 to 8. Preferable is (l) —COOH, —SO$_3$H, or P(O)(OH)$_2$. More preferable is (m) —COOH.

The term "acid linker" in the present specification means a divalent linking group represented by a symbol -(L$^2$)-, and it functions to join 4-position of pyrrolo[2,1-f][1,2,4]triazine nucleus to an "acidic group" in the general relationship. An example of it includes (n) a group represented by the formula:

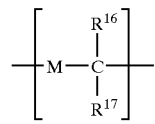

wherein M is —CH$_2$—, —O—, —N(R$^{18}$)—, or —S—wherein R$^{18}$ is a hydrogen atom or C1 to C6 alkyl; R$^{16}$ and R$^{17}$ are independently hydrogen atom, C1 to C10 alkyl, aryl, aralkyl, carboxy, or halogens. Preferable are (o) —O—CH$_2$—, —S—CH$_2$—, —N(R$^{18}$)—CH$_2$—, —CH$_2$—CH$_2$—, —O—CH(CH$_3$)—, or —O—CH((CH$_2$)$_2$Ph)— wherein R$^{18}$ is a hydrogen atom, C1 to C6 alkyl and Ph is phenyl. More preferable is (p) —O—CH$_2$— or —S—CH$_2$—.

In the present specification, the term "acid linker length" means the number of atoms (except for hydrogen atoms) in the shortest chain of a linking group -(L$^2$)- which connects 4-position of pyrrolo[2,1-f][1,2,4]triazine nucleus with the "acidic group". The presence of a carbocyclic ring in -(L$^2$)- counts as the number of atoms approximately equivalent to the calculated diameter of the carbocyclic ring. Thus, a benzene and cyclohexane ring in the acid linker counts as two atoms in calculating the length of -(L$^2$)-. A preferable length is 2 to 3.

A symbol k in the formula (IV) is preferably 1.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or ondensed cyclic aromatic hydrocarbon. An example of the aryl includes phenyl, 1-naphthyl, 2-naphthyl, anthryl and the like. Particularly, phenyl and 1-naphthyl are preferred. Such "aryl" is optionally substituted with C1 to C6 alkyl, hydroxy, C1 to C3 alkyloxy, halogen, nitro, substituted or unsubstituted amino, cyano, C1 to C3 haloalkyl, and the like at one or more position(s).

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl (such as 3-phenylpropyl), naphthylmethyl (such as 1-naphthylmethyl) and the like.

The term "group containing 1 to 4 non-hydrogen atoms" refers to relatively small groups which form substituents at the 6-position of pyrrolo[2,1-f][1,2,4]triazine nucleus, said groups may contain non-hydrogen atoms alone, or non-hydrogen atoms plus hydrogen atoms as required to satisfy the unsubstituted valence of the non-hydrogen atoms, for example; (ii) groups absent hydrogen which contain no more than 4 non-hydrogen atoms such as —$CF_3$, —Cl, —Br, —$NO_2$, —CN, —$SO_3$; and (iii) groups having hydrogen atoms which contain less than 4 non-hydrogen atoms such as —$CH_3$, —$C_2H_5$, —CH=$CH_2$, —CH($CH_3$)$_2$, and cyclopropyl.

An example of the "alkyloxycarbonyl" in the present specification includes methyloxycarbonyl, ethyloxycarbonyl, n-propyloxycarbonyl and the like.

The term "substituted amino" in the present specification includes amino ubstituted with C1 to C6 alkyl, aralkyl, C1 to C6 alkylcarbonyl, C1 to C6 alkyloxycarbonyl, and the like at one or two position(s).

A group of preferable substituents as the $R^1$ to $R^4$ and $R^A$ of the compound represented by the formula (I) will be shown in items (A) to (T). Items (f) to (p) are the same as described above.

As the $R^1$, (A):-($L^1$)-$R^5$, (B):—($CH_2$)$_{1-2}$-(f), (C):—($CH_2$)$_{1-2}$-(g), and (D):—($CH_2$)$_{1-2}$-(h) are preferred.

As the $R^2$, (E): a hydrogen atom, a halogen, C1 to C3 alkyl, C3 to C4 cycloalkyl, or C1 to C3 alkyloxy; and (F): C1 to C3 alkyl or C3 to C4 cycloalkyl are preferred.

As the $R^A$, (G): —C(=O)C(=O)$NH_2$, —$CH_2$C(=O)$NH_2$, or —$CH_2$C(=O)NH$NH_2$, and (H): —C(=O)C(=O)$NH_2$ are preferred.

As the $R^3$, (I):-(n)-(k), (J):-(n)-(l), (K):-(n)-(m), (L):-(o)-(k), (M):-(o)-(l), (N):-(o)-(m), (O):-(p)-(k), (P):-(p)-(l), and (Q):-(p)-(m) are preferred.

As the $R^4$, (R): a hydrogen atom or non-interfering substituent, (S): a hydrogen atom or (i), and (T): a hydrogen atom or (j) are preferred.

A preferred group of compounds represented by the formula (I) is shown below. ($R^1$, $R^2$, $R^A$, $R^4$)=(A, E, G, R), (A, E, G, S), (A, E, G, T), (A, E, H, R), (A, E, H, S), (A, E, H, T), (A, F, G, R), (A, F, G, S), (A, F, G, T), (A, F, H, R), (A, F, H, S), (A, F, H, T), (B, E, G, R), (B, E, G, S), (B, E, G, T), (B, E, H, R), (B, E, H, S), (B, E, H, T), (B, F, G, R), (B, F, G, S), (B, F, G, T), (B, F, H, R), (B, F, H, S), (B, F, H, T), (C, E, G, R), (C, E, G, S), (C, E, G, T), (C, E, H, R), (C, E, H, S), (C, E, H, T), (C, F, G, R), (C, F, G, S), (C, F, G, T), (C, F, H, R), (C, F, H, S), (C, F, H, T), (D, E, G, R), (D, E, G, S), (D, E, G, T), (D, E, H, R), (D, E, H, S), (D, E, H, T), (D, F, G, R), (D, F, G, S), (D, F, G, T), (D, F, H, R), (D, F, H, S), and (D, F, H, T). Preferred embodiments of this invention are compounds wherein $R^3$ is any one of (I) to (Q) and ($R^1$, $R^2$, $R^A$, $R^4$) is any one of the above combinations.

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, chronic rheumatism, arterial sclerosis, stroke, cerebral infarction, heart failure, cardiac infarction, psoriasis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch—Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula (I) in an amount sufficient to inhibit $sPLA_2$ mediated release of fatty acid and to thereby inhibit or prevent the arachidonic acid cascade and its deleterious products.

The term "solvate" includes, for example, solvates with organic solvents, hydrates, and the like.

BEST MODE FOR CARRYING OUT THE INVENTION

The compounds of the invention represented by the formula (I) can be synthesized in accordance with the following method A and B.

(Method A)

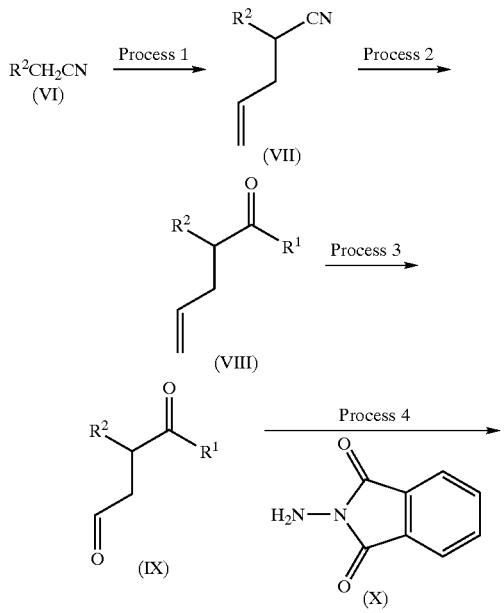

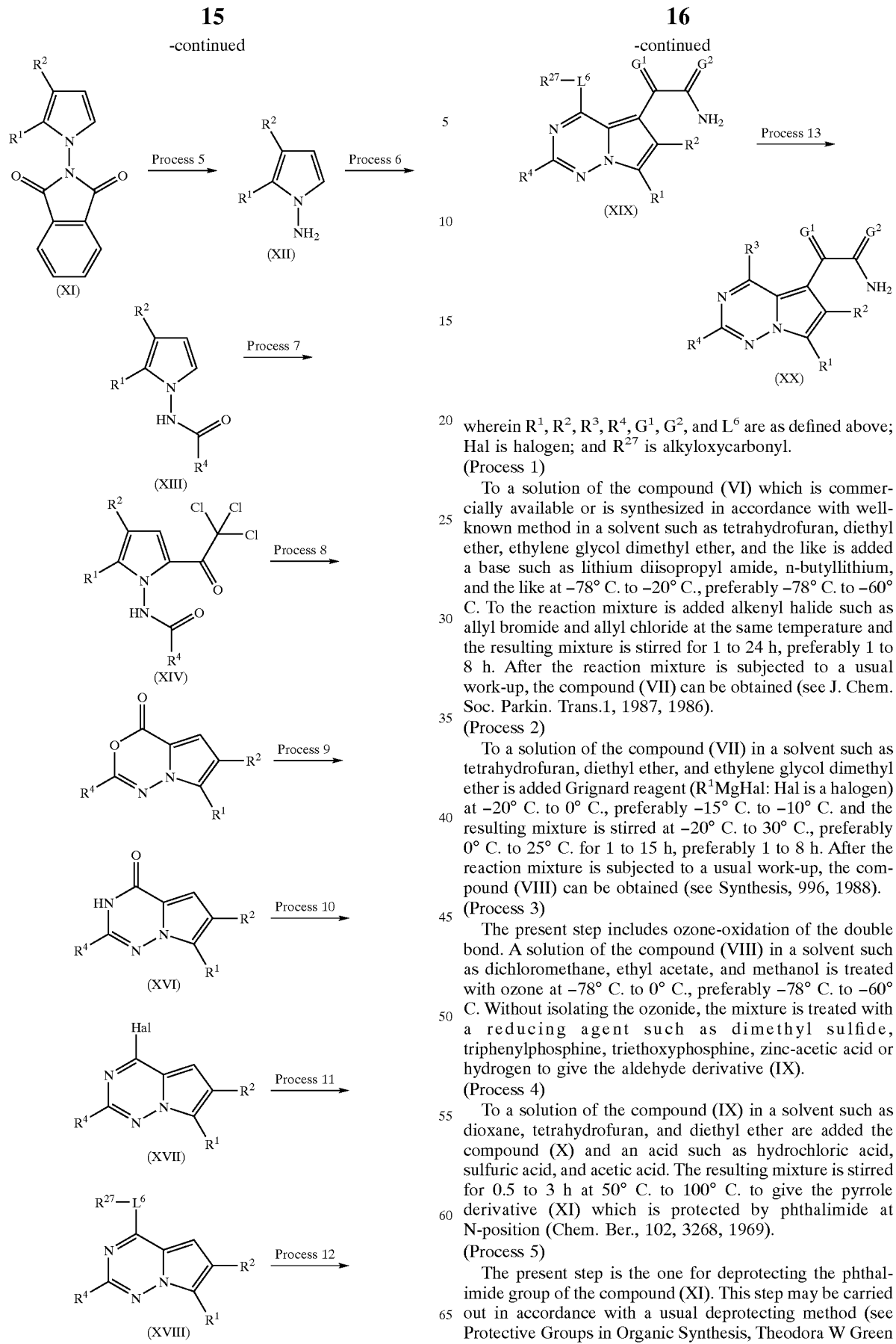

wherein $R^1$, $R^2$, $R^3$, $R^4$, $G^1$, $G^2$, and $L^6$ are as defined above; Hal is halogen; and $R^{27}$ is alkyloxycarbonyl.

(Process 1)

To a solution of the compound (VI) which is commercially available or is synthesized in accordance with well-known method in a solvent such as tetrahydrofuran, diethyl ether, ethylene glycol dimethyl ether, and the like is added a base such as lithium diisopropyl amide, n-butyllithium, and the like at −78° C. to −20° C., preferably −78° C. to −60° C. To the reaction mixture is added alkenyl halide such as allyl bromide and allyl chloride at the same temperature and the resulting mixture is stirred for 1 to 24 h, preferably 1 to 8 h. After the reaction mixture is subjected to a usual work-up, the compound (VII) can be obtained (see J. Chem. Soc. Parkin. Trans.1, 1987, 1986).

(Process 2)

To a solution of the compound (VII) in a solvent such as tetrahydrofuran, diethyl ether, and ethylene glycol dimethyl ether is added Grignard reagent ($R^1$MgHal: Hal is a halogen) at −20° C. to 0° C., preferably −15° C. to −10° C. and the resulting mixture is stirred at −20° C. to 30° C., preferably 0° C. to 25° C. for 1 to 15 h, preferably 1 to 8 h. After the reaction mixture is subjected to a usual work-up, the compound (VIII) can be obtained (see Synthesis, 996, 1988).

(Process 3)

The present step includes ozone-oxidation of the double bond. A solution of the compound (VIII) in a solvent such as dichloromethane, ethyl acetate, and methanol is treated with ozone at −78° C. to 0° C., preferably −78° C. to −60° C. Without isolating the ozonide, the mixture is treated with a reducing agent such as dimethyl sulfide, triphenylphosphine, triethoxyphosphine, zinc-acetic acid or hydrogen to give the aldehyde derivative (IX).

(Process 4)

To a solution of the compound (IX) in a solvent such as dioxane, tetrahydrofuran, and diethyl ether are added the compound (X) and an acid such as hydrochloric acid, sulfuric acid, and acetic acid. The resulting mixture is stirred for 0.5 to 3 h at 50° C. to 100° C. to give the pyrrole derivative (XI) which is protected by phthalimide at N-position (Chem. Ber., 102, 3268, 1969).

(Process 5)

The present step is the one for deprotecting the phthalimide group of the compound (XI). This step may be carried out in accordance with a usual deprotecting method (see Protective Groups in Organic Synthesis, Theodora W Green (John Wiley & Sons)). For example, to a solution of the compound (XI) in an alcohol solvent such as ethanol is added hydrazine and the resulting mixture is stirred at 50° C. to 100° C. for 0.5 to 3 h to give the amino derivative (XII).
(Process 6)

The present step is the one for protecting the amino group with $R^4CO$— wherein $R^4$ is as defined above. The compound (XII) and $R^4CO$-Hal wherein $R^4$ is as defined above and Hal is halogen are reacted in a solvent such as dichloromethane in the presence of a base such as triethylamine and pyridine at −20° C. to 60° C., preferably 0° C. to 30° C. for 1 to 10 h, preferably 1 to 3 h to give the compound (XIII).
(Process 7)

The present step is the one for introducing $Cl_3CCO$— (see Org. Synth., 1988, VI, 618). The compound (XIII) and $Cl_3CCOCl$ are reacted in a solvent such as diethyl ether and tetrahydrofuran at 0° C. to the reflux temperature, preferably at the reflux temperature for 0.5 to 5 h, preferably 0.5 to 1 h to give the compound (XIV).
(Process 8)

The present step is the one for constructing a ring. The compound (XIV) is treated with a base such as potassium carbonate, sodium carbonate, sodium hydroxide, and potassium hydroxide in a solvent such as diethyl ether and tetrahydrofuran at 0° C. to 60° C., preferably 20° C. to 45° C. for 0.5 to 6 h, preferably 0.5 to 3 h to give the compound (XV).
(Process 9)

The present step is the one for re-constructing a ring. The compound (XV) is reacted in ammonium acetate at 120° C. to 180° C., preferably 140° C. to 160° C. for 0.5 to 5 h, preferably 0.5 to 1 h to give the compound (XVI).
(Process 10)

The present step is the one for converting keton into halogen at the 4-position. The compound (XVI) is reacted in a halogenating agent such as phosphorus oxychloride and phenylphosphonic dichloride at 60° C. to the reflux temperature, preferably at the reflux temperature for 0.5 to 6 h, preferably 0.5 to 1 h to give the compound (XVII).
(Process 11)

The present step is the one for converting halogen into $-L^6-R^{27}$ wherein $L^6$ and $R^{27}$ are as defined above at the 4-position. The compound (XVII) and $R^{27}-L^6$-M wherein $L^6$ and $R^{27}$ are as defined above and M is an alkali metal are reacted in a solvent such as diethyl ether and tetrahydrofuran at −20° C. to 60° C., preferably 0° C. to 30° C. for 1 to 8 h, preferably 1 to 3 h to give the compound (XVIII).
(Process 12)

The present step is the one for introducing a substituent to 4-position. To a solution of the compound (XVIII) in a solvent such as toluene, tetrahydrofuran, and 1,2-dichloroethane are added Hal-C(=$G^1$)—C(=$G^2$)-Hal ($G^1$, $G^2$, and Hal are as defined above. For example, oxalyl chloride) and a base such as N-methylmorpholine, triethylamine. The mixture is stirred at 30° C. to 110° C., preferably 65° C. to 110° C. for 1 to 15 h, preferably 1 to 10 h. The reaction mixture is poured into cold aqueous ammonia and the resulting mixture is stirred for 5 to 30 minutes, preferably 10 to 20 minutes to give the compound (XIX).
(Process 13)

The present step is the one for hydrolysis. To a solution of the compound (XIX) in a mixed solvent such as tetrahydrofuran-methanol is added a base such as sodium hydroxide. The resulting mixture is stirred at 0° C. to 40° C., preferably 10° C. to 30° C. for 0.5 to 6 h, preferably 0.5 to 2 h to give the compound (XX).

(Method B)

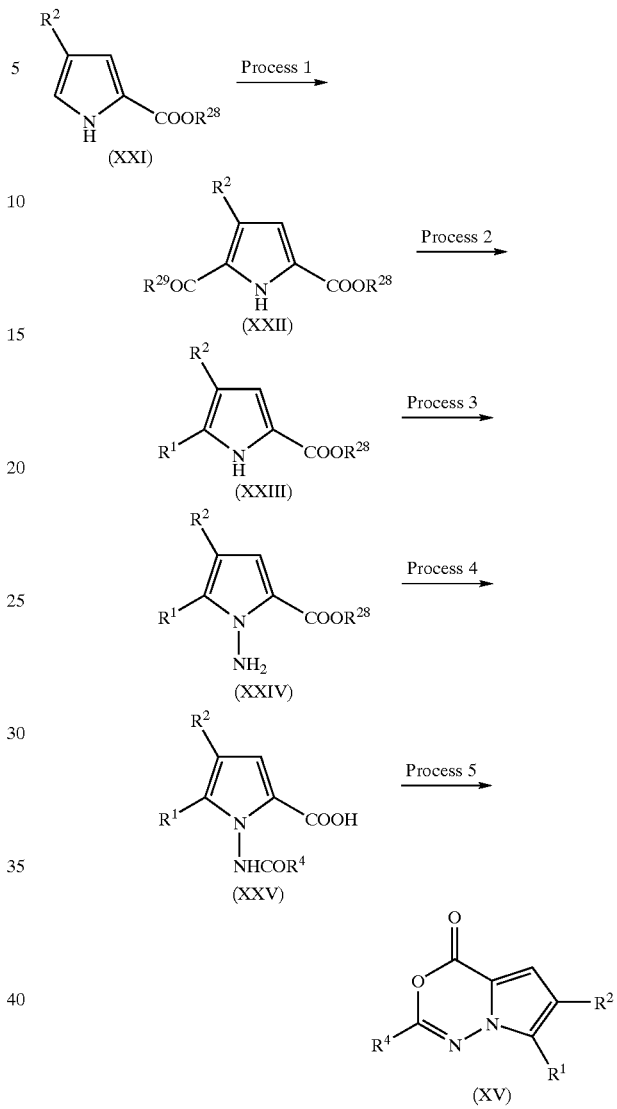

wherein $R^1$, $R^2$, and $R^4$ are as defined above; $R^{28}$ is C1 to C6 alkyl; $R^{29}$ is a precursor of $R^1$)
(Process 1)

The present step is the one for introducing a substituent to 5-position of the pyrrole by Friedel-Crafts reaction. To a solution of the compound (XXI) in a solvent such as 1,2-dichloroethane and dichloromethane are added $R^{29}CO$-Hal wherein $R^{29}$ and Hal are as defined above and Lewis acid such as $AlCl_3$, $SbF_5$, and $BF_3$ at −78° C. to −10° C., preferably −20° C. to 0° C. The resulting mixture is stirred at −10° C. to 10° C., preferably 0° C. to 10° C. for 5 to 30 min, preferably 10 to 20 min to give the compound (XXII). This process can be carried out without using a solvent. For example, the compound (XXI) is dissolved in $R^{29}CO$-Hal and the following part can be done in accordance with the same procedure as described above (J. Med. Chem., 39, 3636–58 (1996)).
(Process 2)

The present step is the one for reducing a carbonyl group at 5-position of the pyrrole to a methylene group. To a solution of Lewis acid such as aluminium chloride in a solvent such as dichloromethane and tetrahydrofuran is added a reducing agent such as sodium borohydride at −20° C. to 10° C., preferably at 0° C. and the resulting mixture is stirred for 5 to 30 min, preferably 10 to 20 min. A solution of the compound (XXII) in a solvent such as dichloromethane and tetrahydrofuran is added to the above reaction mixture at −20° C. to 10° C., preferably at 0° C. The resulting mixture is stirred for 20 to 30 min, preferably 10 to 20 min at the same temperature and additional 1 to 5 h, preferably 2 to 3 h at 15° C. to 40° C., preferably at 20° C. to 30° C. to give the compound (XXIII) (J. Med. Chem., 39, 3636–58 (1996)).

(Process 3)

The present step is the one for amination of the nitrogen atom in the pyrrole ring (J. Heterocycl. Chem. 31 (1994), 4, 781–786). To a suspension of sodium hydride in dimethylformamide are added the compound (XXIII) and O-mesitylenesulfonylhydroxylamine (Synthesis, 140 (1972)) at −20° C. to 60° C., preferably at 0° C. to 30° C. The resulting mixture is stirred for 0.5 to 5 h, preferably 0.5 to 1 h to give the compound (XXIV).

(Process 4)

The present step is the one for introducing $R^4CO$— group to an amino group at 1- position of the pyrrole and hydrolysis of the ester. When two of $R^4CO$— groups are introduced, one of $R^4CO$— group can be removed by the successive hydrolysis. Introducing $R^4CO$— group can be carried out as follows. The compound (XXIV) and $R^4CO$-Hal wherein $R^4$ is as defined above and Hal is halogen are reacted in a solvent such as dichloromethane in the presence of a base such as triethylamine for 0.5 to 6 h, preferably 0.5 to 3 h at 0° C. to 60° C., preferably 10° C. to 30° C. Successively, to a solution of the compound obtained above is added a base such as sodium hydroxide. The resulting mixture is reacted at 10 to 70° C., preferably 50 to 65° C. for 1 to 10 h, preferably 1 to 5 h to yield the compound (XXV).

(Process 5)

The present step is the one for constructing a ring. A solution of the compound (XXV) in acetic anhydride is heated at 80 to 150° C., preferably 130 to 140° C. for 2 to 20 h, preferably 4 to 12 h to yield the compound (XV). The compound (XX) can be obtained from the compound (XV) in a manner similar to those described in the method A—processes 9 to 13.

Where a compound of the present invention has an acidic or basic functional group, a variety of salts having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified stereoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). Ester prodrugs are well known (see, Silverman, Richard B, The Organic Chemistry of Drug Design and Drug Action, Chapter 8, New York, N.Y. Academic Press, ISBN 0-12-643730-0) and are a preferred prodrug form for the compounds of this invention and also for prodrugs used in the method of treating Inflammatory Disease as taught herein. For instance, prodrugs each containing an acid derivative such as an ester which is prepared by reacting a basal acid compound with a suitable alcohol, or an amide which is prepared by reacting a basal acid compound with a suitable amine are well known by those skilled in the art. Aliphatic or aromatic esters derived from acid groups contained in the compounds according to the present invention are preferable prodrugs. Particularly preferred esters as prodrugs are C1 to C6 alkylester and heterocyclic C1 to C6 alkyl ester such as morpholinoethyl ester. For example, methyl ester, ethyl ester, n-propyl ester, isopropyl ester, n-butyl ester, isobutyl ester, tert-butyl ester, morpholinoethyl ester, and N,N-diethylglycolamido ester are exemplified.

Methyl ester prodrugs may be prepared by reaction of the sodium salt of a compound of Formula (I) (in a solvent such as dimethylformamide) with iodo methane (available from Aldrich Chemical Co., Milwaukee, Wis. USA; Item No. 28,956-6).

Ethyl ester prodrugs may be prepared by reaction of the sodium salt of a compound of Formula (I) (in a solvent such as dimethylformamide) with iodo ethane (available from Aldrich Chemical Co., Milwaukee, Wis. USA; Item No. I-778-0).

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinoethyl ester prodrugs may be prepared by reaction of the sodium salt of a compound of Formula (I) (in a medium such as dimethylformamide) with 4-(2-chloroethyl) morpholine hydrochloride (available from Aldrich Chemical Co., Milwaukee, Wis. USA, Item No. C4,220-3).

Double ester such as (acyloxy)alkyl ester or ((alkyloxycarbonyl)oxy)alkyl ester type prodrugs may be optionally manufactured.

The term "inhibit" means that release of fatty acid started by $sPLA_2$ decreases significantly by the compounds of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit $sPLA_2$ inhibiting activity as per the description of the experimental examples which will be described hereinafter. Accordingly, when a curatively effective amount of the compounds represented by the formulae (I), (II), and (III), the prodrug derivatives thereof, or their pharmaceutically acceptable salts, or their solvates is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, stroke, cerebral infarction, inflammatory colitis, psoriasis, heart failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxymethylcellulose solution, or suitable oil, the other compositions can be prepared.

The dosage varies with the conditions of the disease, administration route, age and body weight of patient. In the case of oral administration, the dosage can generally be between 0.01 to 50 mg/kg/day for adult.

The following examples are provided to further illustrate the present invention and are not to be constructed as limiting the scope thereof.

Abbreviations described below are used in the following examples.

Me: methyl
Et: ethyl
Ph: phenyl
Phth: phthaloyl
Ac: Acetyl
Bn: Benzyl
DBU: 1,8-diazabicyclo[5.4.0]-7-undecene

EXAMPLE

Example 1

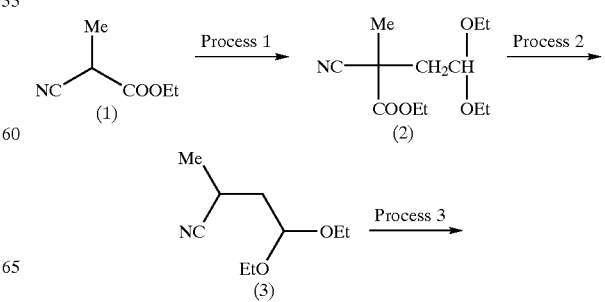

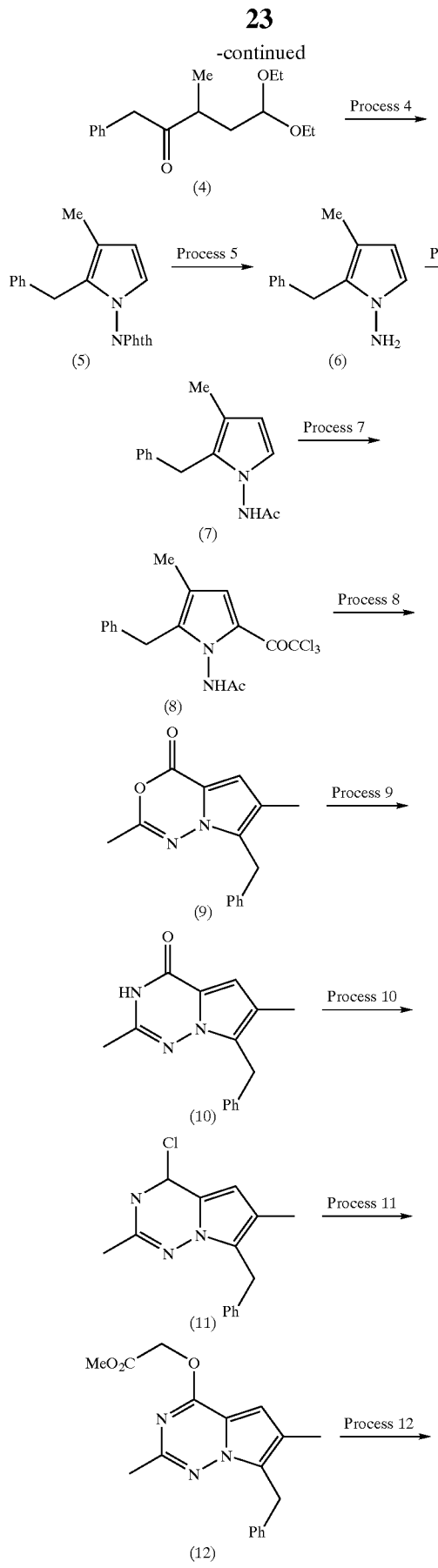

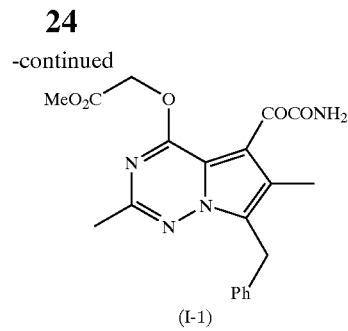

(I-1)

(Process 1)

A mixture of the compound (1) (25.8 g, 0.203 mol), bromoacetaldehydediethyl acetal (48.0 g, 0.244 mol), potassium carbonate (33.7 g, 0.244 mol), and dimethylformamide (130 ml) were heated and stirred for 24 h at 110° C. under nitrogen. The reaction mixture was concentrated under reduced pressure for removing dimethylformamide. To the residue was added water and the mixture was extracted with toluene. The organic layer was washed with water and dried over magnesium sulfate. After removing toluene, the residue was distilled under reduced pressure to give the compound (2) (39.55 g, 80.1%, boiling point 99–102° C. (1 mmHg)) as colorless liquid.

$^1$H-NMR(CDCl$_3$): 1.38(3H, t, J=7.0 Hz), 1.21(3H, t, J=7.0 Hz), 1.62(3H, s), 2.01(1H, m, J=14.2 Hz, J=4.2 Hz), 2.40(1H, m, J=14.2 Hz, J=7.4 Hz), 3.49–3.75(4H, m), 4.24 (1H, q, J=7.0 Hz), 4.25(1H, q, J=7.0 Hz), 4.75(1H, m, J=7.4 Hz, J=4.2 Hz).

(Process 2)

A mixture of the compound (2) (43.6 g, 0.179 mol), potassium acetate (19.3 g, 0.197 mol), and dimethylsulfoxide (87 ml) were heated at 160° C. for 14 h under nitrogen. After cooling, to the reaction mixture was added water and the mixture was extracted with ether. The organic layer was washed with water and dried over magnesium sulfate. After removing solvents, the residue was distilled under reduced pressure to give the compound (3) (29.48 g, 96.0%, boiling point 110–113° C. (23 mmHg)) as colorless liquid.

$^1$H-NMR(CDCl$_3$): 2.13(3H, t, J=7.0 Hz), 1.23(3H, t, J=7.0 Hz), 1.35(3H, d, J=7.6 Hz), 1.73–2.00(2H, m), 2.79 (1H, m), 3.47–3.80(4H, m), 4.67(1H, m).

(Process 3)

To a Grignard reagent which was prepared by magnesium (1.53 g, 0.063 mol), 71 ml of ether, 1,2-dibromoethane (0.26 ml, 0.003 mol), and benzyl bromide (7.14 ml, 0.060 mol) was added a solution of the compound (3) (7.0 g, 0.05 mol) in 35 ml of ether and the resulting mixture was stirred for 4 h at room temperature and heated for 5 h at reflux (60° C.). To the reaction mixture were added an aqueous ammonium chloride (5.35 g, 0.1 mol, 50 ml) under ice-cooling and 63 ml of 2N sulfuric acid and the mixture was stirred for 30 min. The reaction mixture was neutralized by adding sodium bicarbonate (3.36 g, 0.040 mol) and extracted with ether. The organic layer was dried over magnesium sulfate and concentrated in vacuo. The residue was dissolved in toluene and purified by chromatography on silica gel (ethyl acetate:toluene=10:90) to give the compound (4) (9.13 g, 78%).

$^1$H-NMR(CDCl$_3$): 1.11(3H, d, J=7.0 Hz), 1.58–2.24(2H, m), 2.90(1H, m), 3.77(2H, s), 3.78–3.90(4H, m), 4.87(1H, t, J=4.8 Hz), 7.14–7.37(5H, m).

(Process 4)

The compound (4) (35.9 g, 0.129 mol) and N-aminophthalimide (20.9 g, 0.129 mol) were suspended in 95% of ethanol (250 ml). To the suspension was added 1N-hydrochloric acid (13 ml, 0.013 mol) and the resulting mixture was heated for 30 min at reflux. After cooling, the precipitated crystals were filtered to give the compound (5) (35.96 g, 84.4%, melting point 151 to 152° C.) as pale yellow crystals.

Melting point 151 to 152° C.

$^1$H-NMR(CDCl3): 2.13(3H, s), 3.81(2H, s), 6.24(1H, d, J=3.0 Hz), 6.60(1H, d, J=3.0 Hz), 6.92–7.03(5H, m), 7.79 (4H, m).

(Process 5)

The compound (5) (6.0 g, 19 mmol) was dissolved in 60 ml of ethanol, hydrazine monohydrate (2.37 g, 47.4 mmol) was added to the solution, and the mixture was heated for 1 h at reflux. The precipitated were filtered off and the filtrate was concentrated in vacuo for removing ethanol. To the residue was added sat. sodium bicarbonate aq. and the mixture was extracted with ethyl acetate. The organic layer was washed with brine, dried over sodium sulfate, and concentrated in vacuo. The residue was chromatographed on silica gel (ethyl acetate:hexane=20:80) to give the compound (6) (3.21 g, 91%) as yellow oil.

$^1$H-NMR(CDCl$_3$): 2.08(3H, s), 3.98(2H, s), 5.88(1H, s), 6.62(1H, br), 7.09–7.30(5H, m).

(Process 6)

To a solution of the compound (6)(3.2 g, 17.2 mmol) in 50 ml of dichloromethane were added triethylamine (3.6 ml, 25.9 mmol) and acetyl chloride (1.23 ml, 17.3 mmol) and the resulting mixture was stirred for 1 h at room temperature. The reaction mixture was poured into sat. sodium bicarbonate aq. and extracted with chloroform. The organic layer was washed with brine, dried over sodium sulfate, and concentrated in vacuo. The residue was chromatographed on silica gel (ethyl acetate:hexane=40:60) to give the compound (7) (2.67 g, 68%) as colorless crystals.

Melting point 118–119° C.

Elemental Analysis $C_{14}H_{16}N_2O$, Calcd.: C,73.66; H,7.06; N,12.27. Found: C,73.74; H,6.93; N,12.31.

$^1$H-NMR(CDCl$_3$): 1.48 and 1.97(3H, s), 2.09 and 2.15 (3H, s), 3.82 and 3.84(2H, s), 6.02(1H, m), 6.52(1H, m), 7.08–7.29(5H, m), 7.38 and 7.43(1H, br).

(Process 7)

To a solution of the compound (7) (2.64 g, 11.6 mmol) in 50 ml of ether was added trichloroacetyl chloride (1.55 ml, 13.9 mmol) and the mixture was heated at reflux for 45 min. The reaction mixture was poured into sat. sodium bicarbonate aq. and extracted with ethyl acetate. The organic layer was washed with brine, dried over sodium sulfate, and concentrated in vacuo. The residue was chromatographed on silica gel (ethyl acetate:hexane=30:70) to give the compound (8) (3.94 g, 91%) as colorless crystals.

Melting point 142–144° C.

Elemental Analysis $C_{16}H_{15}ClN_2O_2$, Calcd: C, 51.43; H, 4.05; Cl, 28.46; N, 7.50. Found: C, 51.43; H, 4.03; Cl, 28.23; N, 7.59.

$^1$H-NMR(CDCl$_3$): 2.07(3H, s), 2.17(3H, s), 3.93(2H, br), 7.10–7.33(5H, m), 7.73(1H, s), 8.09(1H, br).

(Process 8)

To a solution of the compound (8) (3.9 g, 10.4 mmol) in 40 ml of tetrahydrofuran was added potassium carbonate (3.17 g, 22.9 mmol) and the resulting mixture was stirred for 3 h at 45° C. The reaction mixture was poured into ice-water and extracted with ethyl acetate. The organic layer was washed with brine, dried over sodium sulfate, and concentrated in vacuo. The residue was recrystallized from ethyl acetate-hexane to give the compound (9) (2.65 g, 100%) as colorless crystals.

Melting point 158–159° C.

Elemental Analysis $C_{15}H_{14}N_2O_2$, Calcd: C, 70.85; H, 5.55; N, 11.02. Found: C, 70.66; H, 5.52; N, 10.98.

$^1$H-NMR(CDCl$_3$): 2.13(3H, s), 2.33(3H, s), 4.18(2H, s), 6.96 (1H, s), 7.15–7.31 (5H, m).

(Process 9)

A mixture of the compound (9) (2.65 g, 10.4 mmol) and ammonium acetate (8 g, 104 mmol) was heated at 150° C. for 45 min. After cooling, the reaction mixture was diluted with water. The precipitated powder was filtered off, washed with water, and dried to give the compound (10) (2.48 g, 94%) as white powder.

$^1$H-NMR(d$_6$-DMSO): 2.10(3H, s), 2.21(3H, s), 4.16(2H, s), 6.67(1H, s), 7.15–7.28(5H, m), 11.46(1H, br).

Process 10)

A mixture of the compound (10) (2.48 g, 9.8 mmol) and 10 ml of phosphorus oxychloride was heated at reflux for 30 min. Phosphorus oxychloride was removed under reduced pressure and the residue was diluted with ethtyl acetate. The organic layer was washed with sat. sodium bicarbonate aq. and brine, dried over sodium sulfate, and concentrated in vacuo. The residue was chromatographed on silica gel (ethyl acetate:hexane=10:90) to give the compound (11) (2.42 g, 91%) as orange powder.

Elemental Analysis $C_{15}H_{14}ClN_3$, Calcd: C, 66.30; H, 5.19; Cl, 13.05; N, 15.46. Found: C, 66.52; H, 5.11; Cl, 12.91; N, 15.57.

$^1$H-NMR(CDCl$_3$): 2.29(3H, s), 2.56(3H, s), 4.35(2H, s), 6.75(1H, s), 7.18–7.28(5H, m).

(Process 11)

To a solution of methyl glycolate (4.0 g, 44 mmol) in 30 ml of tetrahydrofuran was added potassium t-butoxide (2.9 g, 25.8 mmol) at ice-cooling and the mixture was stirred for 30 min at room temperature. To the mixture was added the compound (11) (2.34 g, 8.6 mmol) at ice-cooling and the resulting mixture was stirred for 1 h at the same temperature. The reaction mixture was diluted with water and extracted with ethyl acetate. The organic layer was washed with brine, dried over sodium sulfate, and concentrated in vacuo. The residue was chromatographed on silica gel (ethyl acetate:hexane=10:90) to give the compound (12) (2.46 g, 88%) as colorless crystals.

Melting point 109–110° C.

Elemental Analysis $C_{18}H_{19}N_3O_3$, Calcd: C, 66.45; H, 5.89; N, 12.92. Found: C, 66.53; H, 5.89; N, 12.80.

$^1$H-NMR(CDCl$_3$): 2.24(3H, s), 2.41(3H, s), 3.78(3H, s), 4.32(2H, s), 5.05(2H, s), 6.65(1H, s), 7.16–7.27(5H, m).

(Process 12)

To a solution of the compound (12) (695 mg, 2.14 mmol) in 10 ml of toluene were added N-methylmorpholine (2.35 ml, 21.4 mmol) and oxalyl chloride (1.87 ml, 21.4 mmol) and the mixture was heated at reflux for 1.5 h. The resulting mixture was poured into 10 ml of aqueous ammonia (28%) and stirred for 5 min. The mixture was diluted with water and extracted with ethyl acetate. The organic layer was washed with 2N-hydrochloric acid and brine, dried over sodium sulfate, and concentrated in vacuo. The residue was chromatographed on silica gel (ethyl acetate:hexane=90:10) to give the compound (I-1) (361 mg, 43%) as colorless crystals.

Melting point 196–198° C.

Elemental Analysis $C_{20}H_{20}N_4O_5$, Calcd.: C, 60.60; H, 5.09; N, 14.13. Found: C, 60.59; H, 5.04; N, 14.17.

$^1$H-NMR(CDCl$_3$): 2.39(3H, s), 2.46(3H, s), 3.76(3H, s), 4.32(2H, s), 5.03(2H, s), 5.65(1H, br), 6.69(1H, br), 7.18–7.28(5H, m).

Example 2

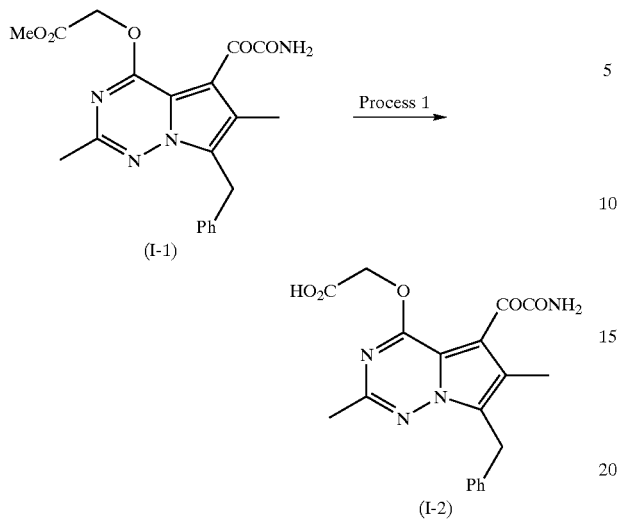

(Process 1)

The compound (I-1) (73 mg, 0.18 mmol) was dissolved in 1.5 ml of methanol and 1.5 ml of tetrahydrofuran, 0.37 ml of 1N sodium hydroxide was added to the solution, and the mixture was stirred for 1.5 h at room temperature. The mixture was acidified with 1 N hydrochloric acid and extracted with ethyl acetate. The organic layer was washed with brine, dried over sodium sulfate, and concentrated in vacuo. The residue was recrystallized from ethyl acetate-hexane to give the compound (I-2) (36 mg, 51%) as colorless crystals.

Melting point 195–197° C.

Elemental Analysis $C_{19}H_{18}N_4O_5$, Calcd.: C, 59.68; H, 4.75; N, 14.65. Found: C, 59.67; H, 4.67; N, 14.61.

$^1$H-NMR($d_6$-DMSO): 2.32(3H, s), 2.42(3H, s), 4.34(2H, s), 4.94(2H, s), 7.19–7.30(5H, m), 7.60(1H, br), 7.99(1H, br), 13.15(1H, br).

Example 3

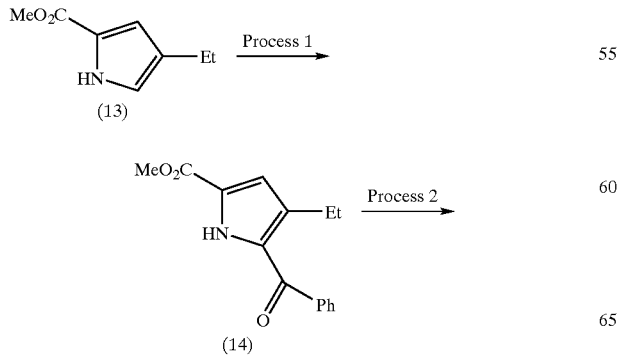

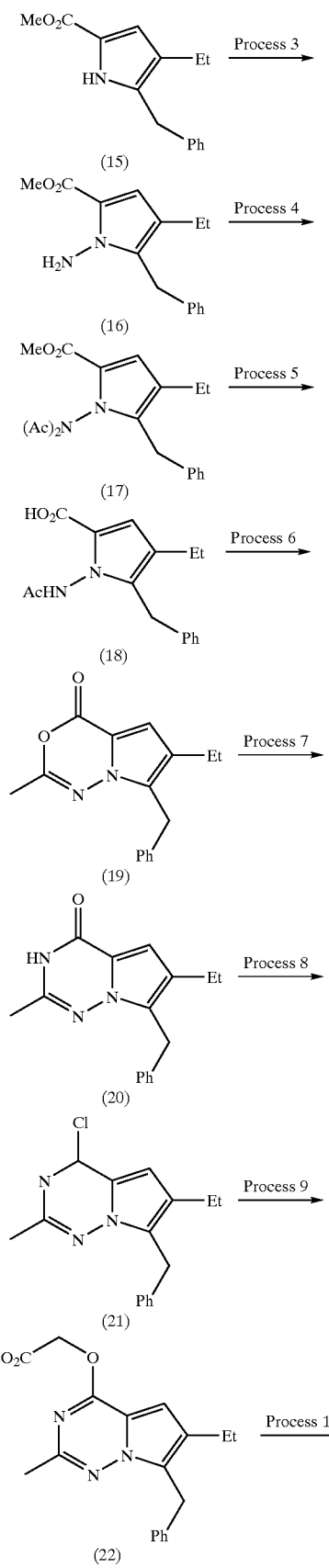

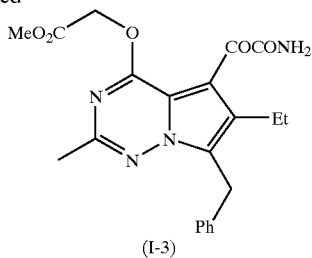

(Process 1)

To a solution of aluminum chloride (7.65 g, 57.4 mmol) in 60 ml of nitromethane was added benzoyl chloride (6.65 ml, 57.3 mmol) dropwise and the mixture was stirred for 15 min at the same condition. To the mixture was added a solution of the compound (13) (2.93 g, 19.1 mmol) which can be synthesized in accordance with the same method describe in Eur. J. Med. Chem., 28,481, (1993) in 40 ml of nitromethane dropwise over 20 min. The resulting mixture was stirred for 30 min at the same condition and additional 30 min at the room temperature. The reaction mixture was poured into ice-water and extracted with ethyl acetate. The organic layer was washed with 28% aqueous ammonia (10 ml), water, and brine, dried over sodium sulfate, and concentrated in vacuo. The residue was chromatographed on silica gel (ethyl acetate:hexane=20:80) to give the compound (14) (4.20 g, 85%) as colorless oil.

$^1$H-NMR(CDCl$_3$): 1.14(3H, t, J=7.5 Hz), 2.55(2H, qd, J=7.5, 0.6 Hz), 3.89(3H, s), 6.85(1H, dt, J=2.7, 0.6 Hz), 7.46–7.53(2H, m), 7.59(1H, m), 7.71(2H, m), 9.48(1H, br).

(Process 2)

To a solution of the compound (14) (776 mg, 3.02 mmol) in 15 ml of methanol was added sodium borohydride (134 mg, 3.55 mmol) at ice-cooling and the resulting mixture was stirred for 20 min at the same condition. Aqueous ammonium chloride was added to the reaction mixture and the resulting mixture was extracted with ethyl acetate. The organic layer was washed with brine, dried over sodium sulfate, and concentrated in vacuo. The obtained crystalline residue was used in the following step without purification.

To a suspension of sodium iodide (2.70 g, 18.0 mmol) in 3 ml of acetonitrile was added chlorotrimethylsilane (2.3 ml, 18.1 mmol) and the mixture was stirred for 15 min at the same condition. To this mixture was added a solution of the residue obtained above step in 9 ml of acetonitrile and the resulting mixture was stirred for 35 min at room temperature. To the reaction mixture was added 10.5 ml of 1N sodium hydroxide and the mixture was extracted with ethyl acetate. The organic layer was washed with 3% sodium thiosulfate aq. and brine, dried over sodium sulfate, and concentrated in vacuo. The residue was chromatographed on silica gel (ethyl acetate:hexane=16:84) to give the compound (15) (647 mg, 88%) as colorless crystals.

$^1$H-NMR(CDCl$_3$): 1.17(3H, t, J=7.5 Hz), 2.45(2H, q, J=7.5 Hz), 3.78(3H, s), 3.94(2H, s), 6.78(1H, d, J=2.7 Hz), 7.12–7.17(2H, m), 7.20–7.34(3H, m), 8.56(1H, br).

(Process 3)

To a suspension of 60% sodium hydride (1.21 g, 30 mmol) in 35 ml of dimethylformamide was added the compound (15) (3.66 g, 15 mmol) at ice-cooling and the mixture was stirred for 15 min at room temperature. To this mixture was added O-mesitylenesulfonylhydroxylamine (4.54 g, 21 mmol) which can be synthesized in accordance with the same method describe in Synthesis, 140 (1972) and the mixture was stirred for 30 min. The reaction mixture was poured into ice water and extracted with ether. The organic layer was washed with brine, dried over sodium sulfate, and concentrated in vacuo. The residue was chromatographed on silica gel (ethyl acetate:hexane=15:85) to give the compound (16) (1.6 g, 41%) as brown oil.

$^1$H-NMR(CDCl$_3$): 1.14(3H, t, J=7.5 Hz), 2.43(2H, q, J=7.5 Hz), 3.80(3H, s), 4.07(2H, s), 6.74(1H, s), 7.10–7.29 (5H, m).

(Process 4)

To a solution of the compound (16) (1.36 g, 5.26 mmol) in 20 ml of dichloromethane were added triethylamine (2.2 ml, 15.8 mmol) and acetyl chloride (0.82 ml, 11.5 mmol) at ice-cooling. The reaction mixture was stirred for 2.5 h at room temperature, poured into ice water, and extracted with chloroform. The organic layer was washed with 10% aqueous hydrochloric acid, sat. sodium bicarbonate aq., and brine, dried over sodium sulfate, and concentrated in vacuo. The residue was chromatographed on silica gel (ethyl acetate:hexane=20:80) to give the compound (17) (1.23 g, 68%) as yellow oil.

$^1$H-NMR(CDCl$_3$): 1.26(3H, t, J=7.5 Hz), 2.01(6H, s), 2.56(2H, q, J=7.5 Hz), 3.74(3H, s), 3.75(2H, s), 6.97(1H, s), 7.08–7.29(5H, m).

(Process 5)

To a solution of the compound (17) (1.2 g, 3.5 mmol) in 5 ml of methanol was added 4.4 ml of 4N sodium hydroxide and the mixture was heated at reflux for 2.5 h. The reaction mixture was acidified with 10% aqueous hydrochloric acid and extracted with ethyl acetate. The organic layer was washed with brine, dried over sodium sulfate, and concentrated in vacuo. The residue was recrystallized from ethyl acetate-hexane to give the compound (18) (840 mg, 84%) as colorless crystals.

Elemental Analysis C$_{16}$H$_{18}$N$_2$O$_3$, Calcd.: C, 67.12; H, 6.34; N, 9.78. Found: C, 66.91; H, 6.37; N, 9.68.

$^1$H-NMR(CDCl$_3$): 1.14(3H, t, J=7.5 Hz), 2.06(3H, s), 2.42(2H, q, J=7.5 Hz), 3.89(2H, s), 6.99(1H, s), 7.07–7.29 (5H, m), 7.92(1H, br).

(Process 6)

The compound (18) (822 mg, 2.87 mmol) was dissolved in 10 ml of acetic anhydride and the mixture was heated at reflux for 4 h. Acetic anhydride was removed, sat. sodium bicarbonate aq. was added to the mixture, and the mixture was extracted with ethyl acetate. The organic layer was washed with brine, dried over sodium sulfate, and concentrated in vacuo. The residue was chromatographed on silica gel (ethyl acetate:hexane=10:90) to give the compound (19) (744 mg, 97%) as white powder.

Elemental Analysis C$_{16}$H$_{16}$N$_2$O$_2$, Calcd.: C, 71.62; H, 6.01; N, 10.44. Found: C, 71.70; H, 6.04; N, 10.45.

$^1$H-NMR(CDCl$_3$): 1.16(3H, t,=7.5 Hz), 2.32(3H, s), 2.51 (2H, q, J=7.5 Hz), 4.19(2H, s), 7.02(2H, s), 7.13–7.29(5H, m).

(Process 7)

A mixture of the compound (19) (733 mg, 2.72 mmol) and ammonium acetate (2.1 g, 27.3 mmol) was heated at 145° C. for 30 min. The reaction mixture was cooled and diluted with water. The precipitated powder was filtered off, washed with water, and dried to give the compound (20) (669 mg, 2.50 mmol) as white powder.

Elemental Analysis C$_{16}$H$_{17}$N$_3$O, Calcd.: C, 71.89; H, 6.41; N, 15.72. Found: C, 71.92; H, 6.45; N, 15.79.

$^1$H-NMR (d$_6$-DMSO): 1.09(3H, t, J=7.5 Hz), 2.21(3H, s), 2.48(2H, q, J=7.5 Hz), 4.18(2H, s), 6.72(1H, s), 7.13–7.28 (5H, m), 11.43(1H, br).

(Process 8)

A mixture of the compound (20) (647 mg, 2.42 mmol) and 3 ml of phosphorus oxychloride was stirred for 30 min at 80°

C. Phosphorus oxychloride was removed under reduced pressure and the residue was diluted with ethyl acetate. The organic layer was washed with sat. sodium bicarbonate aq. and brine, dried over sodium sulfate, and concentrated in vacuo. The residue was chromatographed on silica gel (ethyl acetate:hexane=5:95) to give the compound (21) (644 mg, 93%) as yellow oil.

$^1$H-NMR(CDCl$_3$): 1.24(3H, t, J=7.5 Hz), 2.56(3H, s), 2.67(2H, q, J=7.5 Hz), 4.37(2H, s), 6.80(1H, s), 7.16–7.28 (5H, m).

(Process 9)

To a solution of methyl glycolate (1.0 g, 11.2 mmol) in 10 ml of tetrahydrofuran was added potassium t-butoxide (752 mg, 6.7 mmol) at ice-cooling and the mixture was stirred for 30 min at room temperature. To the reaction mixture was added the compound (21) (638 mg, 2.23 mmol) and the resulting mixture was stirred for 30 min at the same condition. The reaction mixture was diluted with water and extracted with ethyl acetate. The organic layer was washed with brine, dried over sodium sulfate, and concentrated in vacuo. The residue was chromatographed on silica gel (ethyl acetate:hexane=15:85) to give the compound (22) (706 mg, 2.08 mmol) as colorless crystals.

Elemental Analysis C$_{19}$H$_{21}$N$_3$O$_3$, Calcd.: C, 67.24; H, 6.24; N, 12.38. Found: C, 67.30; H, 6.14; N, 12.38.

$^1$H-NMR(CDCl$_3$): 1.20(3H, t, J=7.5 Hz), 2.41(3H, s), 2.62(2H, q, J=7.5 Hz), 3.79(3H, s), 4.33(2H, s), 5.06(2H, s), 6.72(1H, s), 7.16–7.24(5H, m).

(Process 10)

To a solution of the compound (22) (514 mg, 1.51 mmol) in 10 ml of tetrahydrofuran were added N-methylmorpholine (3.3 ml, 30 mmol) and oxalyl chloride (1.95 ml, 22.4 mmol) and the mixture was heated at reflux for 19 h. The resulting mixture was poured into 10 ml of aqueous ammonia (28%) and stirred for 5 min. The mixture was diluted with water and extracted with ethyl acetate. The organic layer was washed with 1N-hydrochloric acid and brine, dried over sodium sulfate, and concentrated in vacuo. The residue was chromatographed on silica gel (ethyl acetate:hexane=70:30) to give the compound (I-3) (182 mg, 29%) as colorless crystals.

Melting point 170–171° C.

Elemental Analysis C$_{21}$H$_{22}$N$_4$O$_5$, Calcd.: C, 61.46; H, 5.40; N, 13.65. Found: C, 61.41; H, 5.43; N, 13.70.

$^1$H-NMR(CDCl$_3$): 1.11(3H, t, J=7.5 Hz), 2.45(3H, s), 2.81(2H, q, J=7.5 Hz), 3.77(3H, s), 4.34(2H, s), 5.02(2H, s), 5.56(1H, br), 6.68(1H, br), 7.15–7.27(5H, m).

Example 4

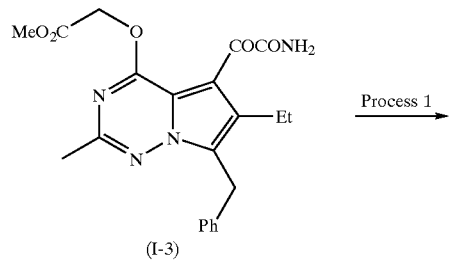
(I-3)

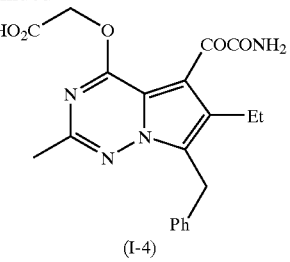
(I-4)

(Process 1)

Using the compound (I-3) as a starting material, compound (I-4) was synthesized in a manner similar to that described in Example 2—Process 1.

Melting point 207–209° C.

Elemental Analysis C$_{20}$H$_{20}$N$_4$O$_5$, Calcd.: C, 60.60; H, 5.09; N, 14.13. Found: C, 60.50; H, 4.96; N, 14.12.

$^1$H-NMR(d$_6$-DMSO): 1.00(3H, t, J=7.5 Hz), 2.42(3H, s), 2.76(2H, q, J=7.5 Hz), 4.35(2H, s), 4.94(2H, s), 7.18–7.30 (5H, m), 7.60(1H, br), 8.01(1H, br).

Example 5

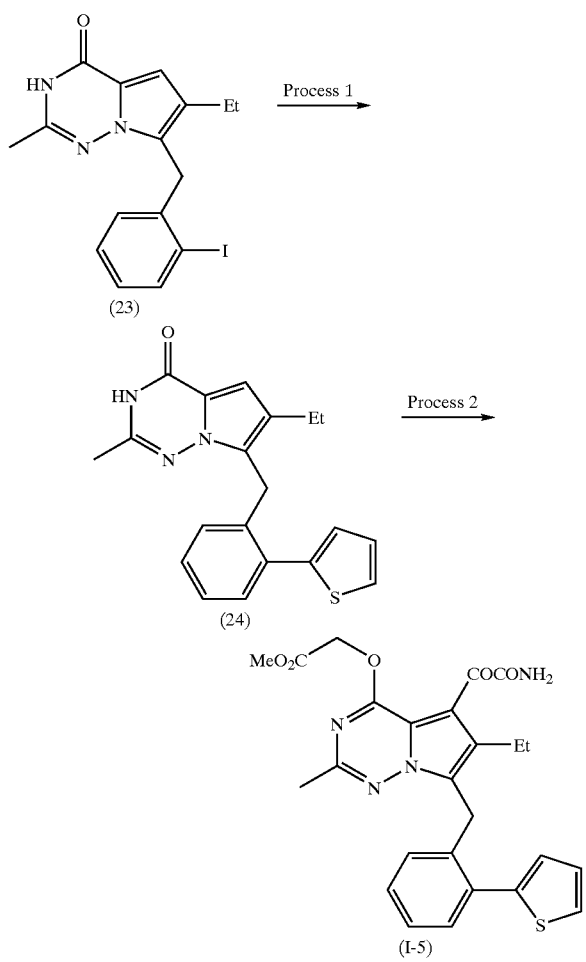

(Process 1)

To a solution of the compound (23) (1.5 g, 3.81 mmol) in 15 ml of dioxane were added tetrakis triphenylphosphine palladium (220 mg, 0.19 mmol), ethanol (7.6 ml), thiophene-2-boronic acid (732 mg, 5.72 mmol), and 2M aqueous sodium carbonate (7.6 ml) and the mixture was heated at reflux for 2 h under argon. The reaction mixture was cooled and acidified with 1N hydrochloric acid. The mixture was diluted with water and precipitated powder were filtered off. The residue was chromatographed on silica gel (methanol:chloroform=3:97) to give the compound (24) (1.12 g, 84%) as white powder.

Elemental Analysis $C_{20}H_{19}N_3OS$, Calcd.: C, 68.74; H, 5.48; N, 12.02; S, 9.18. Found: C, 68.81; H, 5.40; N, 12.00; S, 9.24.

$^1$H-NMR($d_6$-DMSO): 1.00(3H, t, J=7.5 Hz), 2.15(3H, s), 2.29(2H, q, J=7.5 Hz), 4.28(2H, s), 6.72(1H, s), 6.80–7.64 (7H, m), 11.46(1H, br).

(Process 2)

Using the compound (24) as a starting material, compound (I-5) was synthesized in a manner similar to those described in Example 3—Processes 8 to 10.

Melting point 128–129° C.

Elemental Analysis $C_{25}H_{24}N_4O_5S$, Calcd.: C, 60.96; H, 4.91; N, 11.37; S, 6.51. Found: C, 60.90; H, 4.82; N, 11.37; S, 6.53.

$^1$H-NMR(CDCl$_3$): 0.97(3H, t, J=7.5 Hz), 2.41(3H, s), 2.61(2H, q, J=7.5 Hz), 3.78(3H, s), 4.44(2H, s), 5.02(2H, s), 5.57(1H, br), 6.68(1H, br), 6.87–7.41(7H, m).

Example 6

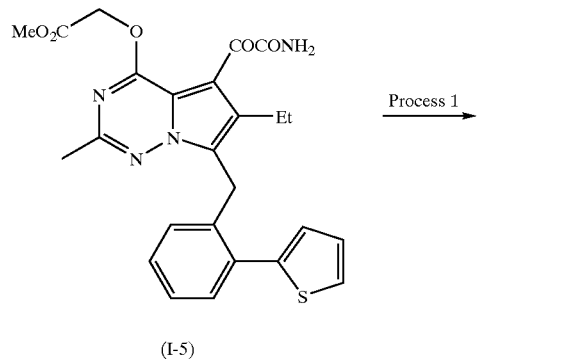

(Process 1)

Using the compound (I-5) as a starting material, compound (I-6) was synthesized in a manner similar to those described in Example 2—Processes 1.

Melting point 184–186° C.

Elemental Analysis $C_{24}H_{22}N_4O_5S$, Calcd.: C, 60.24; H, 4.63; N, 11.71; S, 6.70. Found: C, 60.04; H, 4.39; N, 11.54; S, 6.71.

$^1$H-NMR($d_6$-DMSO): 0.88(3H, t, J=7.2 Hz), 2.35(3H, s), 2.57(2H, q, J=7.2 Hz), 4.44(2H, s), 4.93(2H, s), 6.85–7.62 (7H, m), 7.57(1H, br), 7.97(1H, br).

Example 7 to 8

The compound (I-7) and (I-8) shown in Table 1 were synthesized in a manner similar to that described in Examples 5 and 6. The physical data of each compound are as follows.

TABLE 1

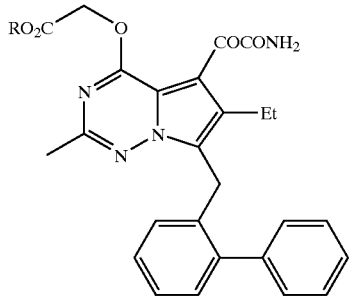

| Compound No. | R | mp (° C.) | $^1$H-NMR (CDCl$_3$) |
|---|---|---|---|
| I-7 | Me | — | 0.93(3H, t, J=7.5Hz), 2.40(3H, s), 2.55 (2H, q, J=7.5Hz), 3.78(3H, s), 4.29(2H, s), 5.01(2H, s), 5.50(1H, br), 6.65(1H, br), 6.95–7.43(9H, m). |
| I-8 | H | 174–176 | 0.91(3H, t, J=7.5Hz), 2.43(3H, s), 2.57 (2H, q, J=7.5Hz), 4.30(2H, s), 5.08(2H, s), 6.93–7.42(10H, m), 7.75(1H, br). |

Test Example

Inhibition Test of Human Secretory Phospholipase $A_2$ Analytical Experiment

In order to identify and evaluate an inhibitor of recombinant human secretory phospholipase $A_2$, the following chromogenic assay is utilized. The assay herein has been applied for high volume screening wherein 96 well microtiterplate is used. A general explanation for such assay is described in "Analysis of Human Synovial Fluid Phospholipase $A_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis: the disclosure of which is incorporated herein for reference.

| Reagents: | |
|---|---|
| (Reaction Buffer) | |
| CaCl$_2$.6H$_2$O | (2.19 g/L) |
| KCl | (7.455 g/L) |
| Bovine Serum Albumin (fatty acid free) (Sigma A-7030) | (1 g/L) |
| Tris-HCl pH 7.5 (adjusted with NaOH) (Enzyme Buffer) | (3.94 g/L) |
| 0.05 M-AcONa 0.2 M-NaCl pH 4.5 (adjusted with acetic acid) (Enzyme Solution) | |

1 mg of sPLA$_2$ is dissolved in 1 ml of an enzyme buffer. Thereafter, the solution is maintained at 4° C.

In the assay, 5 μl of the solution is diluted with 1995 μl of the reaction buffer to be used.

(DTNB)

198 mg of 5,5'-dithiobis-2-benzoic acid (manufactured by Wako Pure Chemicals) is dissolved in 100 ml of H$_2$O pH 7.5 (adjusted with NaOH)
(Substrate Solution)

100 mg of racemic 1,2-bis(heptanoylthio)-1,2-dideoxy-sn-glycero-3-phospholylcholine is dissolved in 1 ml of chloroform.

(Triton-X 100)

624.9 mg of Triton-X 100 is dissolved in the reaction buffer.

Enzyme Reaction: for 1 Plate of Microtiterplate 1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml of the reaction buffer and 0.46 ml of DTNB, and 0.18 ml each of the admixture is poured to wells of the 96 well microtiterplate.
2) 10 μl of a test compound (or solvent blank) are added in accordance with alignment of plates which has been previously set.
3) Incubation is effected at 40° C. for 15 minutes.
4) 20 μl of an enzyme solution (sPLA$_2$) which has been previously diluted (50 ng/well) are added to start reaction (40° C., 30 minutes).
5) Changes in absorbancy for 30 minutes are measured by a plate reader, and inhibition activity was calculated (OD: 405 nm).
6) IC$_{50}$ was determined by plotting log concentration with respect to inhibition values within 10% to 90% inhibiting range.

Results of the human secretory phospholipase A$_2$ inhibition test are shown in the following Table 2.

TABLE 2

| Compound No. | IC$_{50}$ (μM) |
| --- | --- |
| I-1 | 0.203 |
| I-2 | 0.013 |
| I-3 | 0.317 |
| I-4 | 0.011 |
| I-6 | 0.011 |
| I-7 | 0.607 |
| I-8 | 0.008 |

Formulation Example

It is to be noted that the following Formulation Examples 1 to 9 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone | 4 mg |
| (as 10% solution in water) |  |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---|
| Active ingredient | 127 mg |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C, 4 Pa. Thus the lyophilized preparation is obtained.

Industrial Applicability

The compounds according to the present invention have $sPLA_2$ inhibiting activity, so that the compounds of the invention inhibits $sPLA_2$-mediated fatty acid (such as arachidonic acid) release, whereby it is effective for treating septic shock and the like.

What is claimed is:

1. A compound represented by the formula (I):

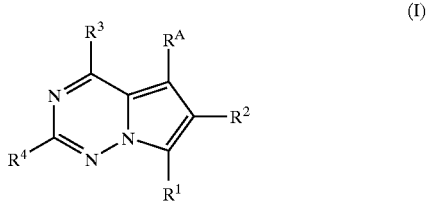

wherein $R^1$ is (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, wherein the non-interfering substituent is selected from C1 to C8 alkyl, C2 to C8 alkenyl, C2 to C8 alkynyl, C7 to C12 aralkyl, C2 to C8 alkenyloxy, C2 to C8 alkynyloxy, C3 to C8 cycloalkyl, C3 to C8 cycloalkenyl, phenyl, tolyl, xylyl, biphenylyl, C1 to C8 alkyloxy, C2 to C12 alkyloxy alkyl, C2 to C12 alkyloxyalkyloxy, C1 to C12 alkylcarbonyl, C1 to C12 alkylcarbonylamino, C1 to C12 alkyloxyamino, C1 to C12 alkyloxyaminocarbonyl, C1 to C12 alkylamino, C1 to C6 alkylthio, C1 to C12 alkylthiocarbonyl, C1 to C8 alkylsulfinyl, C1 to C8 alkylsulfonyl, C2 to C8 haloalkyloxy, C1 to C8 haloalkylsulfonyl, C1 to C8 haloalkyl, C1 to C8 hydroxyalkyl, —C(O)O(C1 to C8alkyl), —(CH$_2$)z-O—(C1 to C8 alkyl) wherein z is an integer from 1 to 8, benzyloxy, aryloxy, arylthio, —(CONHSO$_2$R$^{21}$) wherein $R^{21}$ is C1 to C6 alkyl or aryl, formyl, amino, amidino, halogen, carboxyl, —(CH$_2$)z-COOH wherein z is an integer from 1 to 8, cyano, cyanoguanidino, guanidino, hydrazide, hydrazino, hydroxy, hydroxyamino, nitro, phosphono, —SO$_3$H, carbocyclic groups, and heterocyclic groups, or (c) -(L$^1$)-R$^5$ wherein L$^1$ is a divalent linking group of 1 to 18 atom(s) selected from hydrogen atom(s), nitrogen atom(s), carbon atom(s), oxygen atom(s), and sulfur atom(s), and $R^5$ is a group selected from the groups (a) and (b);

$R^2$ is a hydrogen atom or a group containing 1 to 4 non-hydrogen atoms;

$R^A$ is a group represented by the formula:

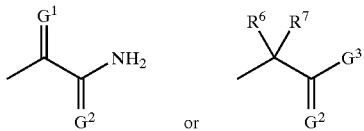

wherein $R^6$ and $R^7$ are independently a hydrogen atom, C1 to C3 alkyl, or a halogen; $G^1$ and $G^2$ are independently an oxygen atom or a sulfur atom; and $G^3$ is —$NH_2$ or —$NHNH_2$;

$R^3$ is -($L^2$)-(acidic group) wherein $L^2$ is an acid linker having an acid linker length of 1 to 5;

$R^4$ is a hydrogen atom, C1 to C6 alkyl aryl, a halogen or aralkyl, its prodrug, their pharmaceutically acceptable salt, or solvate thereof.

2. A compound represented by the formula (II):

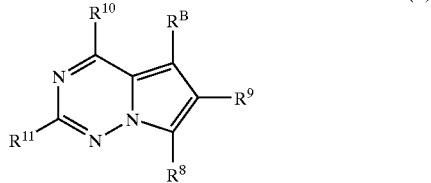

(II)

wherein $R^8$ is —$(CH_2)_m$—$R^{12}$ wherein m is an integer from 1 to 6, and $R^{12}$ is (d) a group represented by the formula:

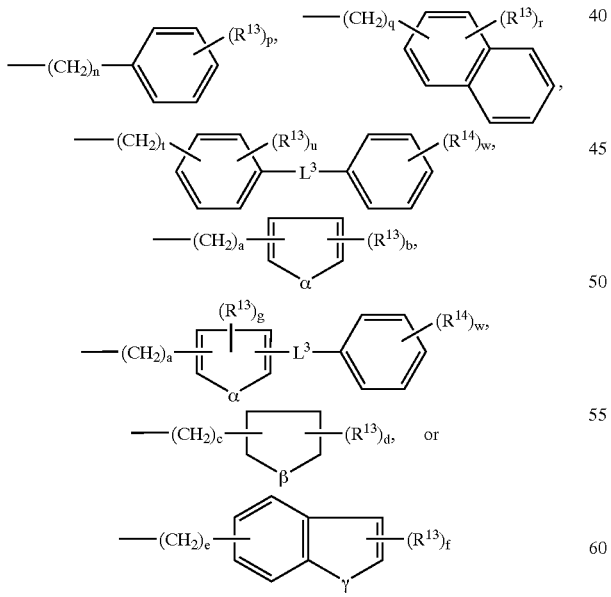

wherein a, c, e, n, q, and t are independently an integer from 0 to 2; $R^{13}$ and $R^{14}$ are independently selected from the group consisting of a halogen, C1 to C10 alkyl, C1 to C10 alkyloxy, C1 to C10 alkylthio, aryl, heterocyclic groups, and C1 to C10 haloalkyl; α is an oxygen atom or a sulfur atom; $L^3$ is —$(CH_2)v$-, —C=C—, —C≡C—, —O—, or —S— wherein v is an integer from 0 to 2; β is —$CH_2$— or —$(CH_2)_2$—; γ is an oxygen atom or a sulfur atom; b is an integer from 0 to 3; d is an integer from 0 to 4; f, p, and w are independently an integer from 0 to 5; g is an integer from 0 to 2; r is an integer from 0 to 7; and u is an integer from 0 to 4, or (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen;

$R^9$ is C1 to C3 alkyl C2 to C3 alkenyl, C3 to C4 cycloalkyl, C3 to C4 cycloalkenyl, C1 to C2 haloalkyl, C1 to C3 alkyloxy, or C1 to C3 alkylthio;

$R^{10}$ is -($L^4$)-$R^{15}$ wherein $L^4$ is represented by the formula:

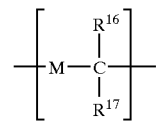

wherein M is —$CH_2$—, —O—, —$N(R^{18})$—, or —S—; $R^{16}$ and $R^{17}$ are independently a hydrogen atom, C1 to C10 alkyl, aryl, aralkyl, carboxy, or a halogen, and $R^{18}$ is a hydrogen atom or C1 to C6 alkyl; and $R^{15}$ is represented by the formula:

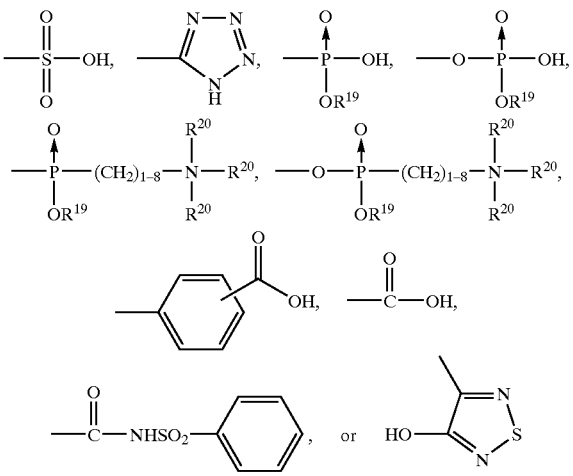

wherein $R^{19}$ is a hydrogen atom, a metal, or C1 to C10 alkyl; $R^{20}$ is independently a hydrogen atom or C1 to C10 alkyl; h is an integer from 1 to 8;

$R^{11}$ is a non-interfering substituent selected from the group consisting of a hydrogen atom, C1 to C8 alkyl, C2 to C8 alkenyl, C2 to C8 alkynyl, C7 to C12 aralkyl, C3 to C8 cycloalkyl, C3 to C8 cycloalkenyl, phenyl, tolyl, xylyl, biphenylyl, C1 to C8 alkyloxy, C2 to C8 alkenyloxy, C2 to C8 alkynyloxy, C2 to C12 alkyloxyalkyl, C2 to C12 alkyloxyalkyloxy, C2 to C12 alkylcarbonyl, C2 to C12 alkylcarbonylamino, C2 to C12 alkyloxyamino, C2 to C12 alkyloxyaminocarbonyl, C1 to C12 alkylamino, C1 to C6 alkylthio, C2 to C12 alkylthiocarbonyl, C1 to C8 alkylsulfinyl, C1 to C8 alkylsulfonyl, C2 to C8 haloalkyloxy, C1 to C8 haloalkylsulfonyl, C2 to C8 haloalkyl, C1 to C8 hydroxyalkyl, —C(O)O(C1 to C8 alkyl), —(CH₂)z-O—(C1 to C8 alkyl), benzyloxy, aryloxy, aryloxy C1 to C8 alkyl, arylthio, arylthio C1 to C8 alkyl, cyano C1 to C8 alkyl, —(CONHSO₂R²¹) wherein R²¹ is C1 to C6 alkyl or aryl, formyl, amino, amidino, halogen, carboxy, —(CH₂)z-COOH wherein z is an integer from 1 to 8, cyano, cyanoguanidyl, guanidino, hydrazide, hydrazino, hydroxy, hydroxyamino, nitro, phosphono, and —SO₃H; and R$^B$ is a group represented by the formula:

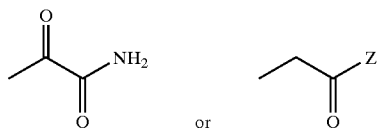

wherein Z is —NH₂ or —NHNH₂, its prodrug, their pharmaceutically acceptable salt, or solvate thereof.

3. A compound, its prodrug, their pharmaceutically acceptable salt, or solvate thereof as claimed in claim 1, wherein said R¹ and R⁸ are represented by the formula:

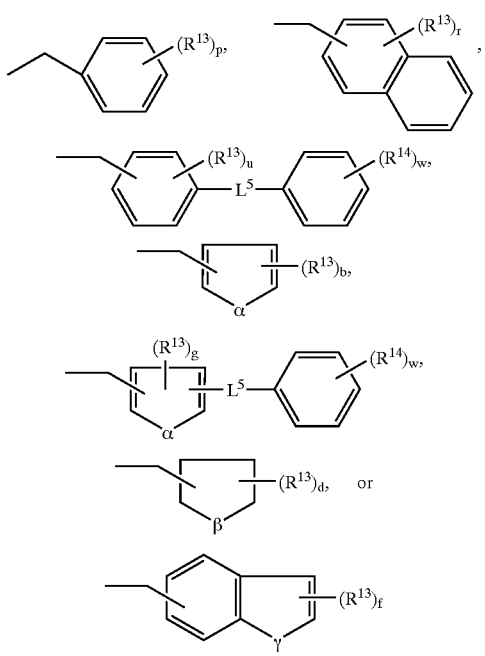

wherein R¹³, R¹⁴, b, d, f, g, p, r, u, w, α, β, and γ are as defined above; L⁵ is a bond, —CH₂—, —C=C—, —C≡C—, —O—, or —S—.

4. A compound, its prodrug, their pharmaceutically acceptable salt, or solvate thereof as claimed in claim 1, wherein said R² and R⁹ are C1 to C3 alkyl or C3 to C4 cycloalkyl.

5. A compound, its prodrug, their pharmaceutically acceptable salt, or solvate thereof as claimed in claim 1, wherein said L² and L⁴ are —O—CH₂—.

6. A compound represented by the formula (III):

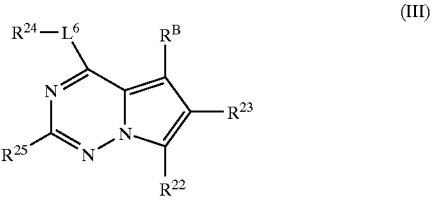

wherein R²² is a group represented by the formula:

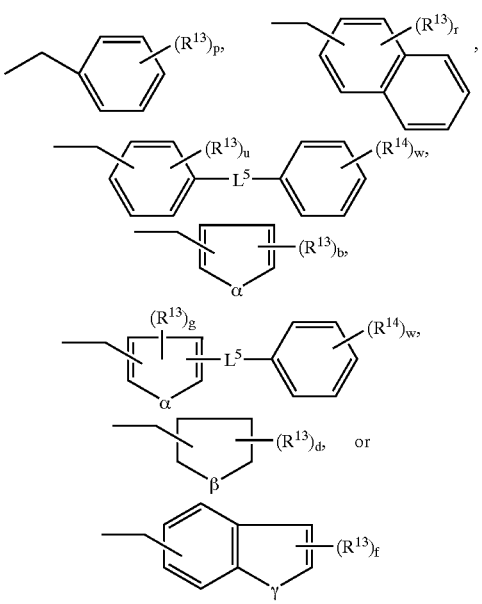

wherein L⁵ is a bond, —CH₂—, —C=C—, —C≡C—, —O—, or —S—; R¹³ and R¹⁴ are independently selected from a group consisting of a halogen, C1 to C10 alkyl, C1 to C10 alkyloxy, C1 to C10 alkylthio, aryl, heterocyclic groups, and C1 to C10 haloalkyl; b is an integer from 0 to 3; d is an integer from 0 to 4; f, p, and w are independently an integer from 0 to 5; g is an integer from 0 to 2; r is an integer from 0 to 7; u is an integer from 0 to 4; α is an oxygen atom or a sulfur atom; β is —CH₂— or —(CH₂)₂—; and γ is an oxygen atom or a sulfur atom;

R²³ is C1 to C3 alkyl or C3 to C4 cycloalkyl;

L⁶ is —O—CH₂—, —S—CH₂, —N(R²⁶)—CH₂—, —CH₂—CH₂—, —O—CH(CH₃)—, or —O—CH((CH₂)₂Ph)— wherein R²⁶ is a hydrogen atom or C1 to C6 alkyl, Ph is phenyl;

R²⁴ is —COOH, —SO₃H, or P(O)(OH)₂;

R²⁵ is a hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, a halogen, carboxy, C1 to C6 alkyloxycarbonyl, aryloxy, aryloxy C1 to C8 alkyl, arylthio, arylthio C1 to C8 alkyl, cyano C1 to C8 alkyl, carbocyclic groups, or heterocyclic groups; and $R^B$ is a group represented by the formula:

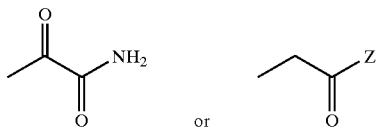

or wherein Z is —NH$_2$ or —NHNH$_2$, its prodrug, their pharmaceutically acceptable salt, or solvate thereof.

7. A compound represented by the formula (IV):

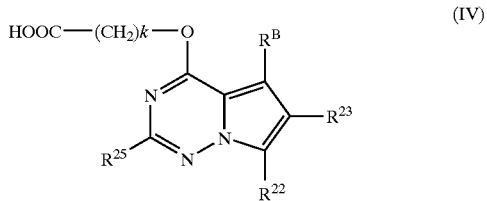

(IV)

wherein $R^{22}$ is a group represented by the formula:

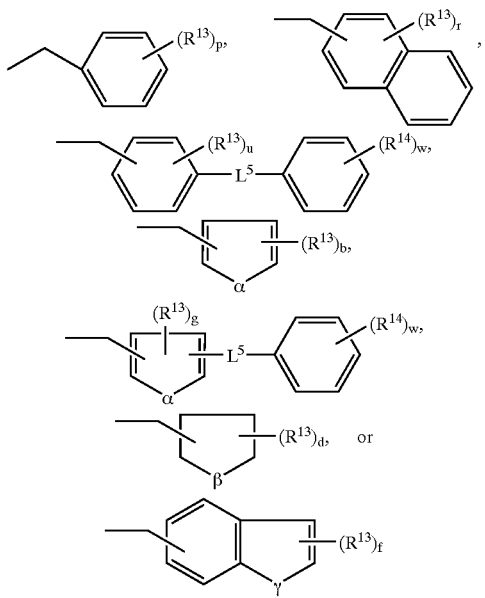

wherein $L^5$ is a bond, —CH$_2$—, —C=C—, —C≡C—, —O—, or —S—; $R^{13}$ and $R^{14}$ are independently selected from the group consisting of a halogen, C1 to C10 alkyl, C1 to C10 alkyloxy, C1 to C10 alkylthio, aryl, heterocyclic groups, and C1 to C10 haloalkyl; b is an integer from 0 to 3; d is an integer from 0 to 4; f, p, and w are independently an integer from 0 to 5; g is an integer from 0 to 2; r is an integer from 0 to 7; u is an integer from 0 to 4; α is an oxygen atom or a sulfur atom; β is —CH$_2$— or —(CH$_2$)$_2$—; and γ is an oxygen atom or a sulfur atom;

$R^{23}$ is C1 to C3 alkyl or C3 to C4 cycloalkyl;

$R^{25}$ is a hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, a halogen, carboxy, C1 to C6 alkyloxycarbonyl, aryloxy, aryloxy C1 to C8 alkyl, arylthio, arylthio C1 to C8 alkyl, cyano C1 to C8 alkyl, carbocyclic groups, or heterocyclic groups;

$R^B$ is a group represented by the formula:

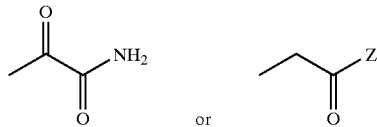

or wherein Z is —NH$_2$ or —NHNH$_2$;

and k is an integer from 1 to 3, its prodrug, their pharmaceutically acceptable salt, or solvate thereof.

8. A compound, its prodrug, their pharmaceutically acceptable salt, or solvate thereof as claimed in claim 6, wherein said $L^6$ is —O—CH$_2$—.

9. A compound, its prodrug, their pharmaceutically acceptable salt, or solvate thereof as claimed in claim 1, wherein said $R^A$ and $R^B$ are —COCONH$_2$.

10. A compound, its prodrug, their pharmaceutically acceptable salt, or solvate thereof as claimed in claim 1, wherein said $R^A$ and $R^B$ are —CH$_2$CONH$_2$.

11. A compound, its prodrug, their pharmaceutically acceptable salt, or solvate thereof as claimed in claim 1, wherein said $R^A$ and $R^B$ are —CH$_2$CONHNH$_2$.

12. A prodrug as claimed in claim 1, wherein the prodrug is an ester prodrug.

13. A pharmaceutical composition containing a compound as claimed in claim 1 as an active ingredient and pharmaceutically acceptable carrier.

14. A method for inhibiting sPLA$_2$, which comprises administering to a mammal a compound as claimed in claim 1 in a pharmaceutically effective amount.

* * * * *